us010034600B2

(12) United States Patent
Igarashi

(10) Patent No.: US 10,034,600 B2
(45) Date of Patent: Jul. 31, 2018

(54) ENDOSCOPE APPARATUS WITH SPECTRAL INTENSITY CONTROL

(71) Applicant: OLYMPUS CORPORATION, Tokyo (JP)

(72) Inventor: Makoto Igarashi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/290,019

(22) Filed: Oct. 11, 2016

(65) Prior Publication Data
US 2017/0027428 A1 Feb. 2, 2017

Related U.S. Application Data

(63) Continuation of application No. PCT/JP2015/074728, filed on Aug. 31, 2015.

(30) Foreign Application Priority Data

Mar. 17, 2015 (JP) ................................ 2015-053688

(51) Int. Cl.
*A61B 1/00* (2006.01)
*A61B 1/04* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC ... A61B 1/00; A61B 1/00006; A61B 1/00009; A61B 1/04; A61B 1/06; A61B 1/0684;
(Continued)

(56) References Cited

U.S. PATENT DOCUMENTS

| 2004/0215060 | A1* | 10/2004 | Ueno ................. A61B 1/00009 600/160 |
| 2007/0153542 | A1 | 7/2007 | Gono et al. |
| 2009/0141125 | A1 | 6/2009 | Yamazaki |
| 2012/0127293 | A1 | 5/2012 | Yamazaki |
| 2013/0265401 | A1 | 10/2013 | Igarashi et al. |

(Continued)

FOREIGN PATENT DOCUMENTS

| CN | 103619233 | * | 3/2014 | ......... A61B 1/00006 |
| EP | 1787577 A1 | | 5/2007 | |

(Continued)

OTHER PUBLICATIONS

Extended Supplementary European Search Report dated Nov. 17, 2017 in European Patent Application No. 15 88 5529.6.

*Primary Examiner* — John P Leubecker
*Assistant Examiner* — William Chou
(74) *Attorney, Agent, or Firm* — Scully, Scott, Murphy & Presser, P.C.

(57) ABSTRACT

An endoscope apparatus includes: a light source section configured to generate first light emitted to a subject having hemoglobin and second light; an image pickup section configured to receive light from the subject irradiated with the light from the light source section to generate an image pickup signal; an image generation section configured to generate an observation image of the subject from a first image pickup signal generated by receiving light from the subject irradiated with the first light and a second image pickup signal generated by receiving light from the subject irradiated with the second light; and a control section configured to control a spectral product of at least one of the first light and the second light such that a spectral product in the wavelength band of the first light falls within 50% to 150% of a spectral product in the wavelength band of the second light.

7 Claims, 13 Drawing Sheets

(51) Int. Cl.
*A61B 1/06* (2006.01)
*G02B 23/24* (2006.01)
*G02B 23/26* (2006.01)
*A61B 5/1459* (2006.01)

(52) U.S. Cl.
CPC ............ *A61B 1/00059* (2013.01); *A61B 1/04* (2013.01); *A61B 5/1459* (2013.01); *G02B 23/24* (2013.01); *G02B 23/2461* (2013.01); *G02B 23/26* (2013.01); *A61B 1/00105* (2013.01); *A61B 1/0684* (2013.01)

(58) Field of Classification Search
CPC .. A61B 5/1459; G02B 23/24; G02B 23/2461; G02B 23/26
USPC ....... 600/109, 113, 160, 178, 179, 180, 181, 600/182; 348/45; 362/574; 382/128, 382/274
See application file for complete search history.

(56) References Cited

U.S. PATENT DOCUMENTS

2013/0324797 A1   12/2013   Igarashi et al.
2017/0006202 A1*   1/2017   Otani .................... H05B 41/38

FOREIGN PATENT DOCUMENTS

| | | |
|---|---|---|
| EP | 2047792 A1 | 4/2009 |
| EP | 2719317 A1 | 4/2014 |
| JP | H07-116115 A | 5/1995 |
| JP | 2006-218283 A | 8/2006 |
| JP | 2008-036035 A | 2/2008 |
| JP | 2009-135907 A | 6/2009 |
| JP | 5404968 B1 | 2/2014 |
| JP | 5427318 B1 | 2/2014 |
| WO | WO 2006025334 A1 | 3/2006 |
| WO | WO 2008015826 A1 | 2/2008 |
| WO | WO 2013145407 A1 | 10/2013 |

* cited by examiner

| DRIVE CURRENTS Ia, Ib | LIGHT EMISSION INTENSITIES | |
|---|---|---|
| | $Ea(\lambda)$ | $Eb(\lambda)$ |
| I1 | Ea1 | Ea1 |
| I2 | Ea2 | Eb2 |
| I3 | Ea3 | Eb3 |
| ⋮ | ⋮ | ⋮ |

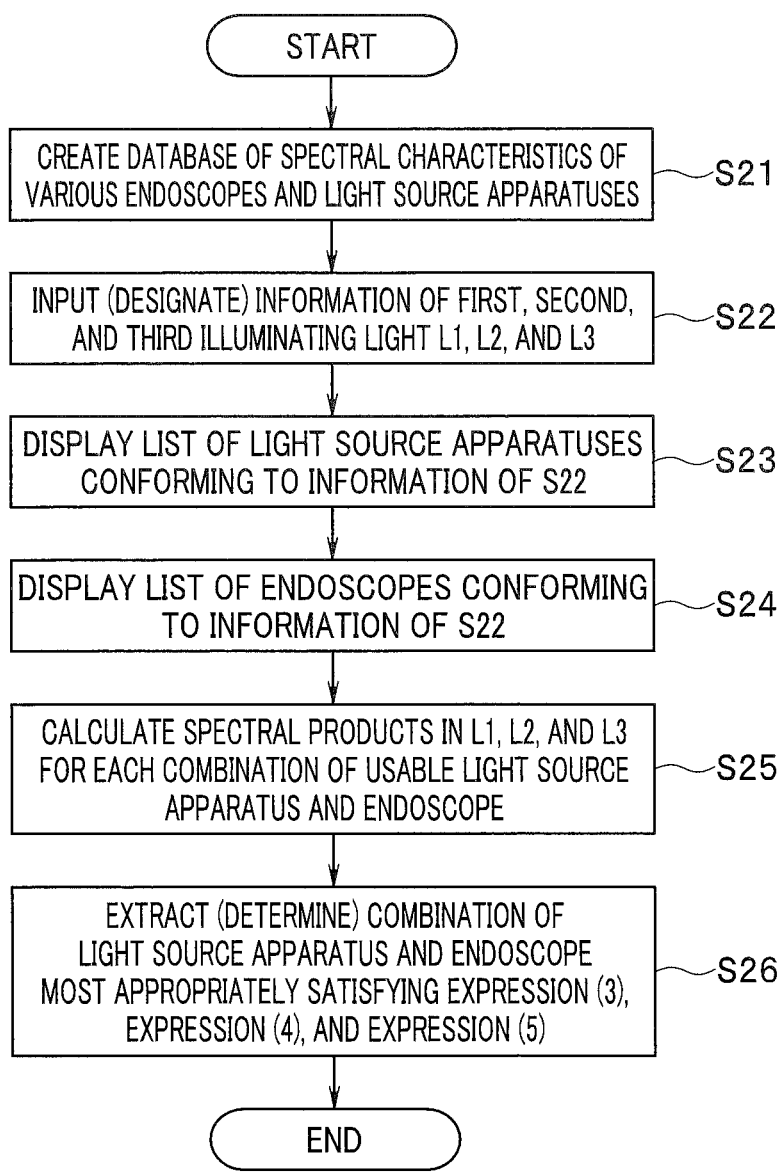

ENDOSCOPE APPARATUS WITH SPECTRAL INTENSITY CONTROL

CROSS REFERENCE TO RELATED APPLICATION

This application is a continuation application of PCT/JP2015/074728 filed on Aug. 31, 2015 and claims benefit of Japanese Application No. 2015-053688 filed in Japan on Mar. 17, 2015, the entire contents of which are incorporated herein by this reference.

BACKGROUND OF THE INVENTION

1. Field of the Invention

The present invention relates to an endoscope apparatus configured to use illuminating light of a plurality of wavelength bands to pick up an image.

2. Description of the Related Art

In recent years, endoscopes configured to inspect inside of subjects are widely used in a medical field and the like. Illumination light of narrow bands of a plurality of wavelength bands is used to pick up an image of a traveling state or the like of blood vessels near a surface layer of a biological tissue to perform endoscopy (or diagnosis) in some cases.

To generate an image by picking up an image of blood vessels near a surface layer of a biological tissue, light of a plurality of wavelength bands, such as light with a wavelength of 600 nm easily absorbed by deep blood vessels near the surface layer and light with a wavelength of 630 nm that is reference light not easily absorbed by the deep blood vessels compared to the light of the wavelength of 600 nm, is used to generate an image emphasizing the deep blood vessels.

In generating such an image, it is difficult to acquire a sufficiently bright image when the reference light is from a visible long wavelength to a near infrared region, because a transmittance of a lens and a sensitivity of image pickup are reduced. Furthermore, balance of light of each wavelength needs to be adjusted to appropriately set color balance, but this is not clearly defined so far.

For example, Japanese Patent Application Laid-Open Publication No. 2009-135907 as a first conventional example is disclosed to provide an image pickup device capable of providing a desirable image with fine color components according to a penetration depth of light in an object, the image pickup device including a light emitting section configured to emit light of first to third wavelength regions (650 nm, 450 nm, and 540 nm) and first to third light receiving elements with sensitivity for the first to third wavelength regions, wherein spectral sensitivities of the respective light receiving elements, a spectral reflectance of the object, and a spectral intensity of light emitted to the object by a light emitting portion are multiplied to obtain values, the values are integrated throughout the wavelength regions to calculate relative light receiving intensities of the respective light receiving elements, and the light receiving elements are arranged on the image pickup device so that the number of first light receiving elements:the number of second light receiving elements:the number of third light receiving elements are 2:2:1 because the relative light receiving intensities are 2:1:1 in the first light receiving elements:the second light receiving elements:the third light receiving elements.

Japanese Patent No. 5404968 as a second conventional example is disclosed to provide an endoscope apparatus capable of clearly displaying blood vessels of a deep part of mucosa at an appropriate brightness without performing cumbersome work of administration of a medicine, wherein narrow band light near the wavelength of 600 nm and narrow band light near the wavelength of 630 nm are emitted, each narrow band signal is multiplied by a light adjustment control parameter, and a largest weight 0.6 is provided to a narrow band signal near the wavelength of 600 nm.

SUMMARY OF THE INVENTION

An aspect of the present invention provides an endoscope apparatus including: a light source section configured to generate light of a first wavelength band emitted to a subject having hemoglobin, the light of the first wavelength band having spectral characteristics of a narrow band between a wavelength including a maximum value and a wavelength including a minimum value on light absorption characteristics of the hemoglobin in a red band of a visible wavelength band, the light source section also configured to generate light of a second wavelength band in which scattering characteristics in the subject and absorption characteristics of the hemoglobin are lower than in the light of the first wavelength band, the light of the second wavelength band including a wavelength band that is a wavelength longer than the light of the first wavelength band; an image pickup section configured to receive light from the subject irradiated with the light from the light source section to generate an image pickup signal; an image generation section configured to generate an observation image of the subject from a first image pickup signal generated by receiving light from the subject irradiated with the light of the first wavelength band and a second image pickup signal generated by receiving light from the subject irradiated with the light of the second wavelength band in the image pickup section; and a control section configured to control a spectral product of at least one of the light of the first wavelength band and the light of the second wavelength band from the light source section to the image pickup section such that a first spectral product from the light source section to the image pickup section in the first wavelength band falls into a condition that is 50% to 150% of a second spectral product from the light source section to the image pickup section in the second wavelength band.

BRIEF DESCRIPTION OF THE DRAWINGS

FIG. 13 is a flowchart showing a process of determining a combination of an endoscope and a light source apparatus suitable for predetermined endoscopy in performing the endoscopy.

DETAILED DESCRIPTION OF THE PREFERRED EMBODIMENT(S)

Hereinafter, embodiments of the present invention will be described with reference to the drawings.

First Embodiment

Figure 1:
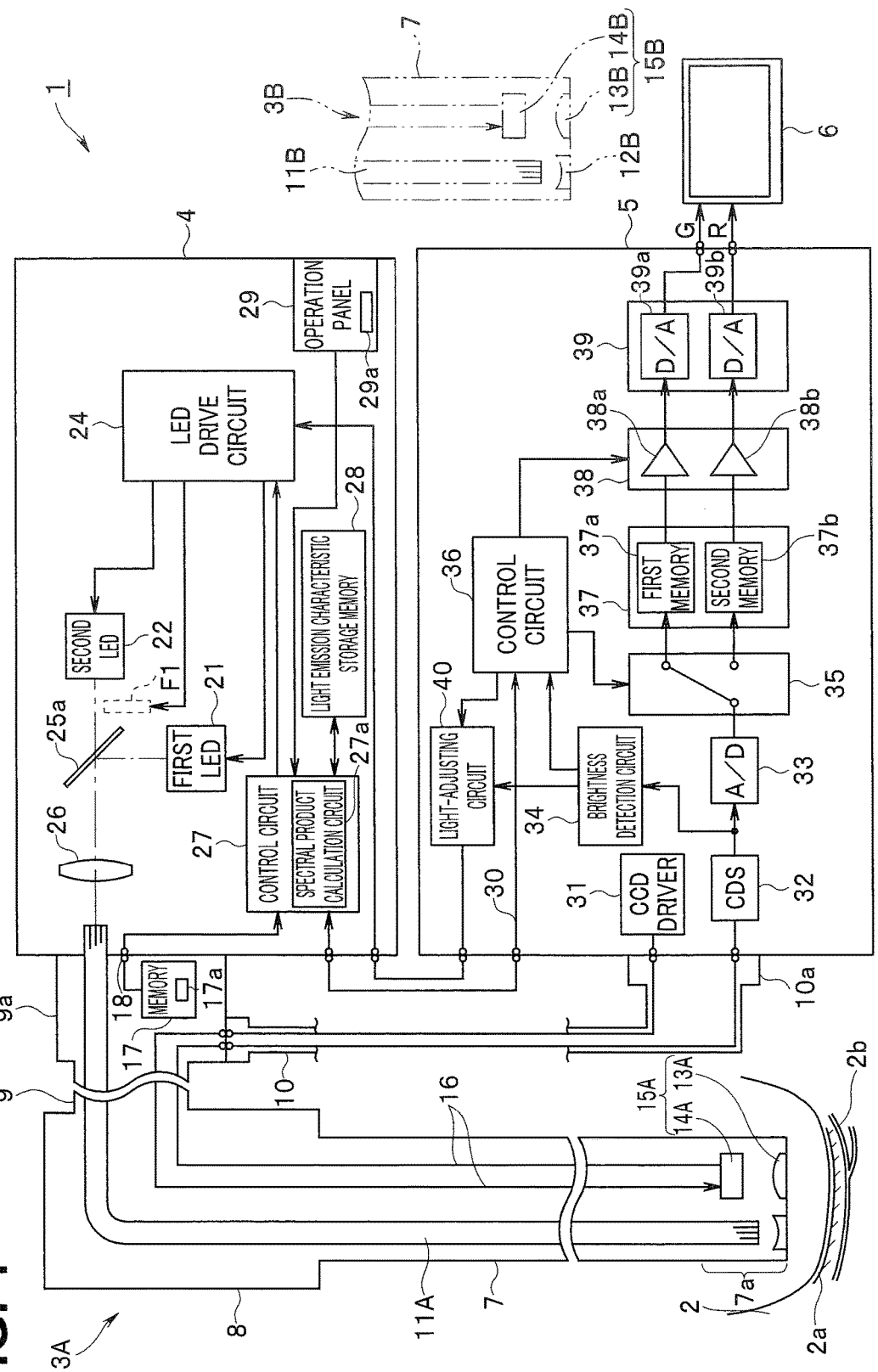
FIG. 1 is a diagram showing an overall configuration of an endoscope apparatus of a first embodiment of the present invention.

As shown in FIG. 1, an endoscope apparatus 1 of a first embodiment of the present invention includes: an endoscope 3A inserted into a subject 2; a light source apparatus 4 to which the endoscope 3A is detachably connected, the light source apparatus 4 forming a light source section configured to generate and output illuminating light; a video processor 5 to which a signal connector 10a of the endoscope 3A is detachably connected, the video processor 5 forming an image generation section configured to execute signal processing for an image pickup device mounted on the endoscope 3A and generate an observation image (image signal of the observation image) of the subject 2; and a color monitor 6 as a display apparatus configured to receive the image signal outputted from the video processor 5 to display the observation image.

Note that as shown in FIG. 1, the endoscope apparatus 1 can also perform endoscopy for the subject 2 by using an endoscope 3B provided with an image pickup device and the like with optical characteristics different from those of the image pickup device and the like mounted on the endoscope 3A.

The endoscope 3A includes: an elongated insertion portion 7; an operation portion 8 provided on a back end (proximal end) of the insertion portion 7; and a universal cable 9 extended from the operation portion 8. A light source connector 9a is provided on an end portion of the universal cable 9, and the light source connector 9a is detachably connected to the light source apparatus 4. One end of a cable 10 is connected to the light source connector 9a, and the signal connector 10a on the other end of the cable 10 is detachably connected to the video processor 5.

A light guide 11A configured to transfer (guide) illuminating light is inserted into the endoscope 3A, and a back end of the light guide 11A reaches the light source connector 9a. The back end of the light guide 11A is an incident end of the illuminating light, and the illuminating light is supplied from the light source apparatus 4. The illuminating light incident on the light guide 11A further passes through an illumination lens 12A attached to an illumination window from a distal end surface of the light guide 11A arranged on a distal end portion 7a of the insertion portion 7, and the illuminating light is emitted toward the subject 2.

An objective lens 13A is attached to an observation window adjacent to the illumination window, and for example, a charge coupled device (abbreviated as CCD) 14A as an image pickup device is arranged on an image formation position of the objective lens 13A. The objective lens 13A and the CCD 14A form an image pickup section (or an image pickup unit) 15A. Note that the endoscope 3B includes a CCD 14B with characteristics different from those of the CCD 14A and the like in the endoscope 3A. More specifically, the endoscope 3B includes a light guide 11B, an illumination lens 12B, an objective lens 13B, the CCD 14B, and an image pickup section 15B with characteristics different from those of the endoscope 3A, and the other components are the same as in the endoscope 3A.

Although the characteristics of the endoscope 3B are different from those of the endoscope 3A, the endoscope 3B can be connected to the light source apparatus 4 and the video processor 5 as in the case of the endoscope 3A and can be similarly used for endoscopy. Therefore, in the following description, the case of the endoscopy 3A will be mostly described. This is substantially the same in a second embodiment.

The CCD 14A is connected to signal lines 16 located in the cable 10 in the endoscope 3A and is electrically connected to the video processor 5 through the signal connector 10a.

A flash memory (simply abbreviated as a memory in FIG. 1) 17 storing identification information (abbreviated as ID) unique to the endoscope 3A is provided in, for example, the light source connector 9a in the endoscope 3A, and the flash memory 17 can read out the ID in the flash memory 17 from a control circuit in the light source apparatus 4 through a contact point 18.

The light source apparatus 4 includes: a first light emitting diode (abbreviated as LED) 21 forming a first illuminating light source (or a first light emitting element) configured to generate first illuminating light as illuminating light of a first wavelength band; a second LED 22 forming a second illuminating light source (or a second light emitting element) configured to generate second illuminating light as illuminating light of a second wavelength band; and an LED drive circuit 24 configured to drive the LEDs 21 and 22 to emit the light and halt the light emission.

Figure 5:
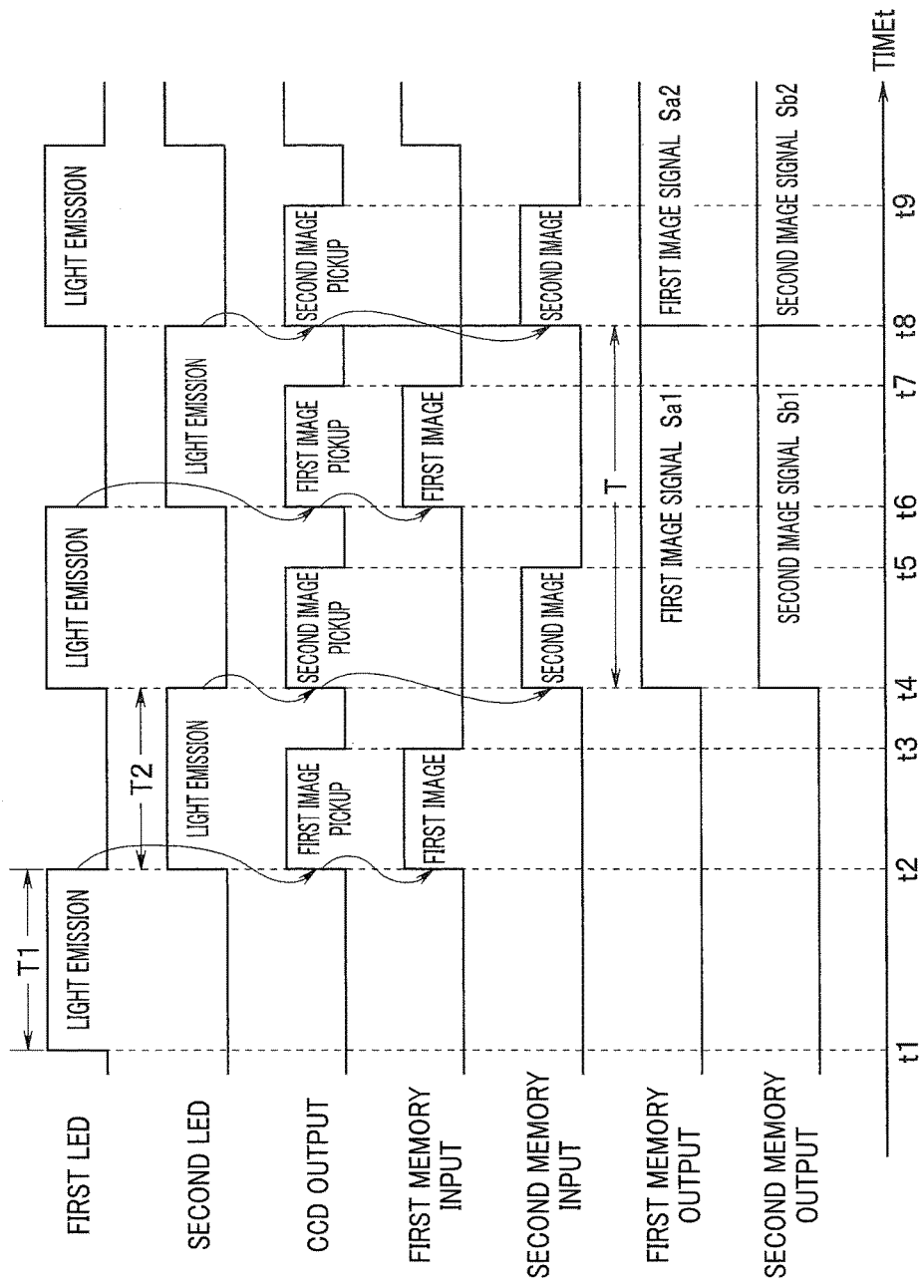
FIG. 5 is a timing diagram showing operation in performing the endoscopy in the first embodiment.

Note that as shown in FIG. 5 described later, the LED drive circuit 24 drives the LEDs 21 and 22 to perform frame-sequential illumination for alternate light emission. The CCD 14A forms a monochrome image pickup device configured to pick up an image under the frame-sequential illumination by the LEDs 21 and 22.

A dichroic mirror 25a arranged on an illuminating light path of the first illuminating light generated by the first LED 21 selectively reflects the first illuminating light in the first wavelength band. The first illuminating light is condensed by a condensing lens 26 arranged on a reflected light path, and the first illuminating light enters an incident end of the light guide 11A.

The dichroic mirror 25a arranged on an illuminating light path of the second illuminating light generated by the second LED 22 selectively transmits the second illuminating light in the second wavelength band. The second illuminating light is condensed by the condensing lens 26 arranged on a transmission optical path, and the second illuminating light enters the incident end of the light guide 11A.

Figure 2:
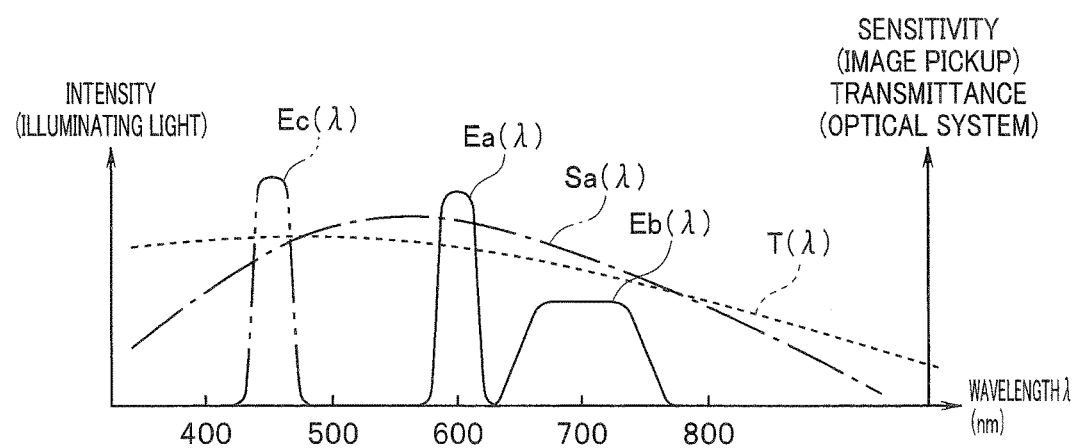
FIG. 2 is a diagram showing spectral characteristics of light emission intensities of respective light emitting elements of a light source section, an image pickup sensitivity of an image pickup device, and a transmittance of an optical system, such as a light guide, with respect to wavelengths in the first embodiment.

In FIG. 2, each solid line shows a light emission intensity (or spectral radiance) Ea ($\lambda$) of narrow band light near 600 nm that is the first illuminating light (that is, light of the first wavelength band with a center wavelength of 600 nm) and a light emission intensity (or spectral radiance) Eb ($\lambda$) of wide band light as light of the second wavelength band near 630 nm to 780 nm that is the second illuminating light (band from red to near infrared). In FIG. 2, an alternate long and two short dashes line shows a light emission intensity (or spectral radiance) Ec ($\lambda$) of narrow band light near 460 nm that is third illuminating light described later. Note that Ea ($\lambda$) that changes depending on a wavelength $\lambda$ is abbreviated as Ea in some cases (the same applies to Eb ($\lambda$) and like, and Sa ($\lambda$) and T ($\lambda$) are also simply shown as Sa and T in some cases).

The light emission intensities Ea ($\lambda$) and Eb ($\lambda$) shown in FIG. 2 show characteristics of cases in which the LEDs 21 and 22 are driven to emit light based on drive currents Ia and Ib near maximum values, respectively, and values of the drive currents Ia and Ib can be changed to change peak values and the like.

Figures 3A, 3B:
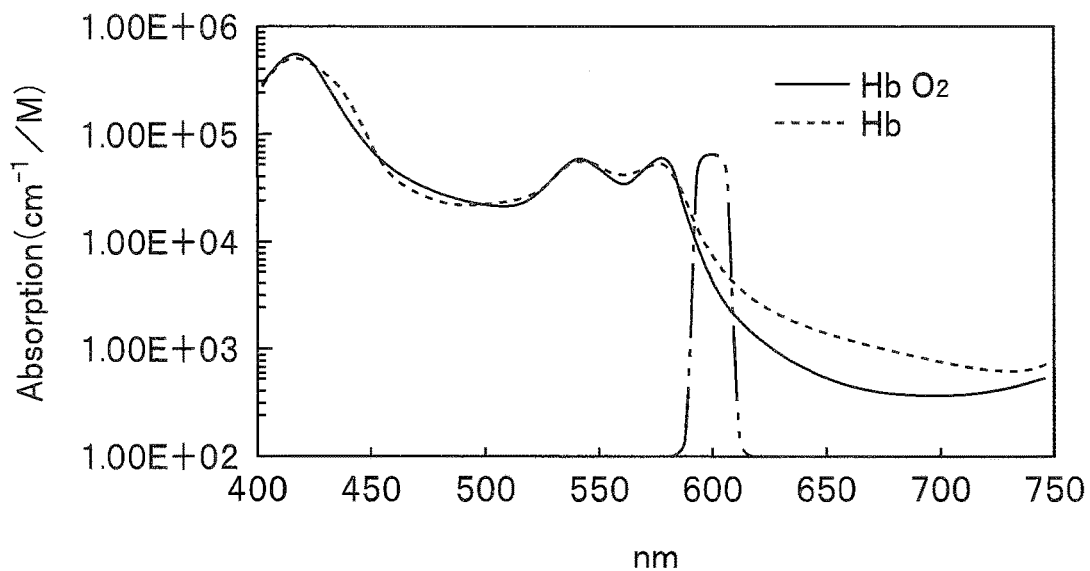
FIG. 3A is a diagram showing light absorption characteristics of oxyhemoglobin and deoxyhemoglobin.
FIG. 3B is a diagram showing a look-up table associating drive currents stored in advance in a memory in a light source apparatus and characteristics of the light emission intensities.

Note that the present embodiment is designed to acquire an observation image that facilitates treatment or the like of a traveling state or the like of blood vessels near a surface layer of a biological mucosa in the subject 2. In this case, capillaries 2a travel near the surface in the biological mucosa as shown in FIG. 1, and thicker blood vessels 2b travel on a deeper side. In the treatment, it is desirable to be able to observe the traveling state of the blood vessels 2b with an excellent image quality. FIG. 3A shows light absorption characteristics of oxyhemoglobin (HbO2) and deoxyhemoglobin (Hb), and an alternate long and two short dashes line shows a narrow band light near 600 nm that is the first illuminating light.

In the narrow band light near 600 nm that is the first illuminating light, the light absorption characteristics of hemoglobin included in the blood in the blood vessels are large. On the other hand, the light absorption characteristics of hemoglobin are low (compared to the first illuminating light) in wide band light on a longer wavelength side than 630 nm that is the second illuminating light. In addition, scattered scattering characteristics of the second illuminating light are lower than those of the first illuminating light (penetration depth on the deep side in the biological mucosa is high). In other words, the narrow band light near 600 nm is light of a first wavelength band emitted to a subject having hemoglobin, the light having spectral characteristics of a narrow band between a wavelength including a maximum value and a wavelength including a minimum value on the light absorption characteristics of the hemoglobin in a red band of a visible wavelength band.

Therefore, the observation image generated by picking up images by using both of the first illuminating light and the second illuminating light includes a first image (components) and a second image (components).

In the observation image, the traveling state of the thick blood vessels 2b can be figured out from a change in a contrast of the first image components picked up under the first illuminating light, and an outline and the like of a background part from the surface layer region to the deep region can be figured out from the second image components picked up under the second illuminating light.

In FIG. 2, an alternate long and short dash line shows an image pickup sensitivity (or a spectral sensitivity) Sa ($\lambda$) of the CCD 14A. In FIG. 2, a dotted line shows a spectral transmittance (or a transmittance) T of an illuminating light transfer system/image pickup optical system including: an illuminating light transfer system (or an illuminating light guide system) configured to optically transfer the first illuminating light and the second illuminating light and emit the light to the subject 2; and an image pickup optical system (or an objective optical system) configured to cause light scattered by the subject 2 side to enter the CCD 14A as an image pickup device. Note that the illuminating light transfer system includes the dichroic mirror 25a and the condensing lens 26 in the light source apparatus 4, the light guide 11A of the endoscope 3A, and the like. Therefore, the spectral transmittance T is a product of a spectral transmittance Tls of the light source apparatus 4 and a spectral transmittance Ten of the endoscope 3A as described later.

The light source apparatus 4 includes a control circuit 27 including a central processing unit (CPU) or the like forming a control section configured to control operation of the LED drive circuit 24, and the control circuit 27 refers to information of a light emission characteristic storage memory 28 storing light emission characteristics of the first LED 21 and the second LED 22. The light emission characteristic storage memory 28 includes, for example, a flash memory or the like as a non-volatile memory that allows rewriting the stored data (information).

FIG. 3B shows an example of the light emission characteristics of the first LED 21 and the second LED 22 stored in advance in the light emission characteristic storage memory 28. As shown in FIG. 3B, values of the drive currents Ia and Ib and the light emission intensities are stored as a look-up table (abbreviated as LUT). Note that the LUT of FIG. 3 indicates that the light emission intensities of the LEDs 21 and 22 are Ea1 and Eb1 when the drive currents Ia and Ib for respectively causing the LEDs 21 and 22 to emit light are set to, for example, a drive current value I1.

The data of the light emission characteristics of FIG. 3B can be referenced to calculate two spectral products A1 and A2 of equation (1) and equation (2) described later, and an adjustment can be made so that the two spectral products A1 and A2 can satisfy a predetermined relationship as shown in expression (3).

As described later, when illuminating light of a plurality of wavelength bands (first and second illuminating light in the present embodiment) is used in initial setting before performing the endoscopy by the endoscope apparatus 1 to perform the illumination and the image pickup in the present embodiment, the spectral product or the light emission characteristics (mainly light emission intensity) forming the spectral product are adjusted for the illuminating light of at least one wavelength band so that the spectral product of each wavelength band satisfies a predetermined condition to make the image quality of the observation image displayed on the display apparatus greater than a predetermined image quality. A control section configured to control the adjustment is formed by the control circuit 27.

The control circuit 27 includes a spectral product calculation circuit 27a configured to calculate the respective spectral products A1 and A2 for the illuminating light of the first and second wavelength bands.

To allow the spectral product calculation circuit 27a to calculate the spectral products A1 and A2, the flash memory 17 provided in the endoscope 3A includes, for example, a spectral information storage region 17a storing information of the spectral sensitivity Sa ($\lambda$) of the CCD 14A as an image pickup device mounted on the endoscope 3A and the overall spectral transmittance Ten ($\lambda$) including each spectral transmittance of the light guide 11A, the illumination lens 12A, and the objective lens 13A in the endoscope 3A. The endoscope 3B includes a spectral information storage region 17b (not shown) corresponding to the endoscope 3B.

The light emission characteristic storage memory 28 in the light source apparatus 4 stores the characteristics of the light emission intensities Ea and Eb of the LEDs 21 and 22 described above and stores the information of the spectral transmittances Tls (λ) of the dichroic mirror 25a and the condensing lens 26.

The spectral product calculation circuit 27a refers to the information to calculate the first spectral product A1 in the image pickup by the CCD 14A for the first illuminating light of the first wavelength band as follows.

$$A1 = \int Sa(\lambda) Ea(\lambda) Tls(\lambda) Ten(\lambda) d\lambda \qquad (1)$$

Note that the integration is performed in the first wavelength band of the first illuminating light.

Similarly, the spectral product calculation circuit 27a calculates the second spectral product A2 as follows.

$$A2 = \int Sb(\lambda) Eb(\lambda) Tls(\lambda) Ten(\lambda) d\lambda \qquad (2)$$

In a case of an endoscope not storing the spectral information in the flash memory 17, the information of the spectral sensitivity of the image pickup device mounted on the endoscope and the spectral transmittances of the light guide and the like can be inputted to the control circuit 27 from an information input portion (or an information input device) 29a of an operation panel 29 (formed by a keyboard and the like) provided on the light source apparatus 4, for example.

The control circuit 27 can use the information inputted from the operation panel 29 to calculate the spectral products even if the endoscope does not store the spectral information.

The video processor 5 includes a CCD driver 31 configured to apply a CCD drive signal to the CCD 14A, and when the CCD drive signal is applied, the CCD 14A outputs an image pickup signal obtained by photoelectrically converting an optical image formed on an image pickup surface of the CCD 14A. The CCD driver 31 outputs the CCD drive signal in synchronization with the end of each illumination period (light emission period) of the first illuminating light and the second illuminating light. Therefore, the CCD 14A alternately outputs a first image pickup signal and a second image pickup signal (see FIG. 5).

The image pickup signals outputted from the CCD 14A are inputted to a correlated dual sampling circuit (abbreviated as CDS circuit) 32 in the video processor 5. The CDS circuit 32 extracts signal components of the image pickup signals (first and second image pickup signals) and output the signal components as image signals (first and second image signals) to an A/D conversion circuit 33 and a brightness detection circuit 34.

The A/D conversion circuit 33 converts an analog image signal to a digital image signal and outputs the signal to a multiplexer 35.

The multiplexer 35 is switched by a control circuit 36 in the video processor 5 in synchronization with the switch of the illumination periods of the first illuminating light and the second illuminating light. The image signals (first and second image signals) outputted from the multiplexer 35 are alternately stored in respective first memory 37a and second memory 37b included in a memory circuit 37. The image signals (first and second image signals) stored in the first memory 37a and the second memory 37b are read out at the same time and are inputted to variable gain amplifiers 38a and 38b forming a color balance circuit 38 configured to set (adjust) color balance. Note that the color balance circuit 38 may be arranged on a former stage of the memory circuit 37.

The image signals (first and second image signals) passing through the color balance circuit 38 are converted to analog image signals (first and second image signals) through D/A conversion circuits 39a and 39b forming a D/A conversion section 39, and the signals are outputted as image signals of the observation image to channels G and R of the color monitor 6.

The brightness detection circuit 34 calculates average brightness of each of the inputted image signals (first and second image signals) in one frame period or the like and outputs signals of the calculated average brightness (brightness signals) to a light-adjusting circuit 40 configured to adjust light.

The light-adjusting circuit 40 generates a light adjustment signal that is a signal of a difference value of reference brightness and one overall brightness signal obtained by adding the inputted two average brightness signals at a predetermined ratio and outputs the generated light adjustment signal to the LED drive circuit 24 in the light source apparatus 4. Note that the brightness detection circuit 34 may generate the overall brightness signal.

Before the endoscopy is performed, the brightness detection circuit 34 sends, to the control circuit 36, a brightness signal of the first image signal and a brightness signal of the second image signal generated when a standard white plate is set on the object. The control circuit 36 adjusts gains of the variable gain amplifiers 38a and 38b of the color balance circuit 38 to set a color balance state in which a luminance level of the first image signal and a luminance level of the second image signal outputted from the color balance circuit 38 are equal.

The LED drive circuit 24 adjusts amounts of light emission of the LEDs 21 and 22 to make the inputted light adjustment signal small. The adjustment of the amounts of light emission can maintain an illumination state that allows obtaining reference brightness in which the light adjustment signal is almost 0.

The control circuit 36 in the video processor 5 is connected to the control circuit 27 in the light source apparatus 4 through a communication line 30 and is capable of performing two-way transmission and reception of signals through the communication line 30.

The control circuit 27 (the spectral product calculation circuit 27a of the control circuit 27) has a function of calculating the first and second spectral products A1 and A2 and has a function of a judgement circuit configured to judge whether the two spectral products satisfy the following predetermined condition.

$$0.5 \leq A1/A2 \leq 1.5 \qquad (3)$$

The condition of expression (3) is equivalent to the condition for making the image quality of the observation image generated by using the light of a plurality of wavelength bands equal to or greater than a predetermined image quality as a whole. In other words, when the condition of expression (3) is satisfied, the observation image holds an excellent image quality equal to or greater than the predetermined image quality as a whole.

If 1.5<A1/A2 that is an example of a case not satisfying the condition of expression (3), the image pickup sensitivity of the image pickup device (CCD 14A) and the transmission characteristics of the optical system, such as the light guide 11A, do not vary much between the first wavelength band and the second wavelength band (characteristic diagram of FIG. 2). Therefore, a ratio of the light emission intensity Ea of the LED 21 contributing to the spectral product A1 is significantly greater than a ratio of the light emission intensity Eb of the LED 22 contributing to the spectral product A2. In other words, an area of the light emission intensity Eb of the LED 22 in FIG. 2 is significantly smaller than an area of the light emission intensity Ea of the LED 21.

Therefore, a signal level of the second image signal is significantly smaller than a signal level of the first image pickup signal obtained by the CCD 14A as an image pickup device.

Therefore, the color balance circuit 38 can compensate the signal level by making the gain of the variable gain amplifier 38$b$ configured to adjust the signal level of the second image signal corresponding to the second image pickup signal much greater than the gain of the variable gain amplifier 38$a$ configured to adjust the signal level of the first image signal corresponding to the first image pickup signal. However, the noise also increases in this case. As a result, an S/N (or an SNR) of the second image signal becomes significantly lower than an S/N of the first image signal.

That is, if 1.5<A1/A2, the image quality of the second image components of the first image components and the second image components forming the observation image is reduced by the noise.

On the other hand, if 0.5>A1/A2 that is an example of a case not satisfying the condition of expression (3), the image quality of the first image components of the first image components and the second image components forming the observation image is reduced by the noise as can be understood from the description above.

Although the brightness of the observation image is adjusted by the light adjustment signal, a variable range of the first illuminating light is restricted to smaller values if 0.5>A1/A2. This results in a drawback that the first image (components) in the observation image becomes dark (when an AGC not shown is provided, the image quality of the first image is reduced by the noise as described above).

The endoscope apparatus 1 of the present embodiment includes: the light source apparatus 4 forming a light source section configured to generate narrow band light near 600 nm emitted to the subject 2 having hemoglobin, the narrow band light forming light of a first wavelength band including spectral characteristics of a narrow band between a wavelength including a maximum value and a wavelength including a minimum value on light absorption characteristics of the hemoglobin in a red band of a visible wavelength band, the light source section configured to also generate light of a second wavelength band in which scattering characteristics in the subject and absorption characteristics of the hemoglobin are lower than in the light of the first wavelength band, the light of the second wavelength band including a wavelength band of 630 nm to 780 nm that is a wavelength longer than the light of the first wavelength band; the image pickup section 15A or 15B configured to receive light from the subject 2 irradiated with the light from the light source section to generate a first image pickup signal that is an image pickup signal of the subject 2 corresponding to the light of the first wavelength band and a second image pickup signal that is an image pickup signal of the subject 2 corresponding to the light of the second wavelength band; the video processor 5 twilling an image generation section configured to generate an observation image of the subject 2 from the first image pickup signal and the second image pickup signal generated by the image pickup section 15A or 15B; and the control circuit 27 forming a control section configured to control a value of a spectral product of at least one of the light of the first wavelength band and the light of the second wavelength band from the light source section to the image pickup section 15A or 15B such that the first spectral product A1 from the light source section to the image pickup section 15A or 15B in the first wavelength band falls within 50% to 150% (that is, 0.5≤A1/A2≤1.5) of the second spectral product A2 from the light source section to the image pickup section 15A or 15B in the second wavelength band. In the present embodiment, when the control section controls the value of at least one of the spectral products, the control section controls or adjusts the light emission intensity (more accurately, light emission characteristics or spectral characteristics including the light emission intensity or bandwidth) of the light source configured to generate the light of the second wavelength band contributing to the spectral product A2, for example.

Figure 4:
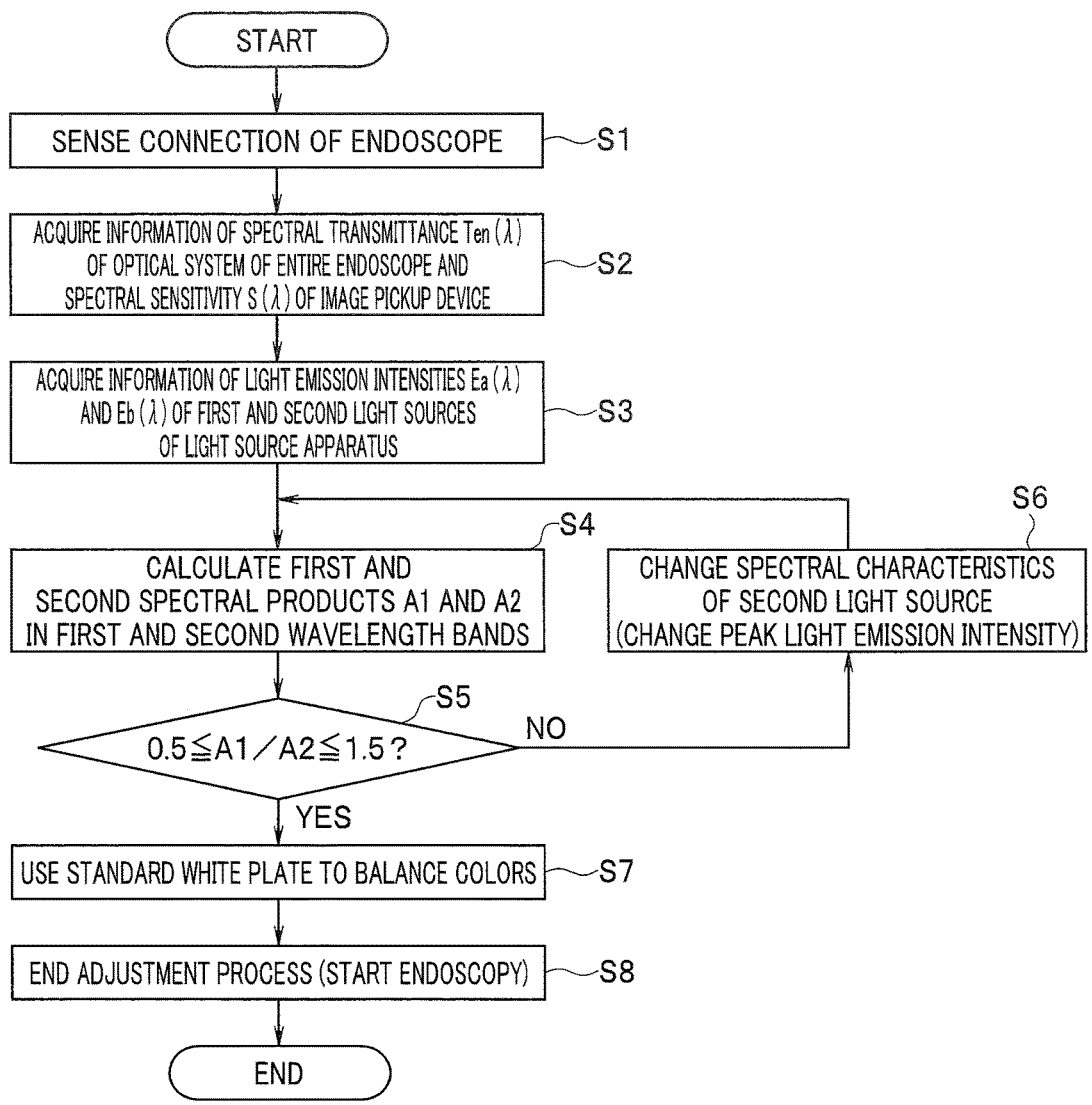
FIG. 4 is a flowchart showing content of an adjustment process before endoscopy of the first embodiment.

Next, an action of the present embodiment will be described. FIG. 4 shows a process of adjusting the endoscope apparatus 1 to a state that allows acquiring an observation image with a desirable image quality as a whole before the endoscopy is performed.

An operator connects the endoscope 3A to the light source apparatus 4 and the video processor 5 as shown in FIG. 1, arranges the standard white plate in front of the distal end portion 7$a$ of the endoscope 3A, and turns on the power source of the endoscope apparatus 1 (the light source apparatus 4, the video processor 5, and the color monitor 6 forming the endoscope apparatus 1).

Consequently, the control circuit 27 of the light source apparatus 4 is activated, and in first step S1, the control circuit 27 reads out the ID of the flash memory 17 to sense (identify) the endoscope 3A connected to the light source apparatus 4. Note that the operator may input an instruction for reading out the ID or the like of the endoscope 3A connected to the light source apparatus 4.

In step S2, the control circuit 27 reads out the information of the spectral information storage region 17$a$ of the flash memory 17 to acquire the information of the spectral transmittance Tls ($\lambda$) of the optical system of the entire endoscope and the information of the spectral sensitivity S ($\lambda$) of the CCD 14A as an image pickup device.

In step S3, the control circuit 27 acquires the information of the light emission intensities Ea ($\lambda$) and Eb ($\lambda$) of the LEDs 21 and 22 forming first and second light sources from the spectral characteristic storage memory 28 in the light source apparatus 4. The control circuit 27 also acquires the information of the spectral transmittance Tls ($\lambda$) of the optical system in the light source apparatus 4.

In next step S4, the control circuit 27 uses the information acquired in steps S2 and S3 to calculate the first and second spectral products A1 and A2 in the first and second wavelength bands. Note that in the calculation of the first and second spectral products A1 and A2, values in the case of light emission based on drive currents (Ia=Ias, Ib=Ibs) in a standard state are used as the information of the light emission intensities Ea ($\lambda$) and Eb ($\lambda$), for example.

In next step S5, the control circuit 27 judges whether the calculated first and second spectral products A1 and A2 satisfy the condition of expression (3), that is, 0.5≤A1/A2≤1.5.

If the judgement result indicates that the condition of expression (3) is not satisfied in the judgement process of step S5, the control circuit 27 changes the light emission intensity Eb ($\lambda$) of the LED 22 that is the second light source in step S6 and returns to the process of step S4.

For example, if the judgement result indicates 0.5>A1/A2, the control circuit 27 reduces the value of the drive current Ib for causing the LED 22 to emit light through the LED drive circuit 24 in step S6. Note that as indicated by a dotted line in FIG. 1, a band restriction filter F1 configured to restrict transmission of light of part of the wavelength band in the second wavelength band emitted by the LED 22 may be inserted onto the optical path to reduce the second spectral product A2.

On the other hand, if the judgement result indicates 1.5<A1/A2, the control circuit 27 increases the value of the drive current Ib for causing the LED 22 to emit light through the LED drive circuit 24 in step S6. In this way, the control circuit 27 performs the control to make an adjustment such that the spectral products A1 and A2 satisfy the condition of expression (3). Note that when the adjustment cannot be made to satisfy the condition of expression (3) within the variable range of the drive current Ib for causing the LED 22 to emit light, the light emission intensity (light emission characteristics) of the LED 21 is changed to make an adjustment to satisfy the condition of expression (3).

For example, if the judgement result is still 0.5>A1/A2 even when the value of the drive current Ib for causing the LED 22 to emit light is set to a lower limit value of the variable range, the value of the drive current Ia is adjusted to increase the light emission intensity (tight emission characteristics) of the LED 21 to make an adjustment to satisfy the condition of expression (3).

If the judgement result is still 1.5<A1/A2 even when the value of the drive current Ib for causing the LED 22 to emit light is set to an upper limit value of the variable range, the value of the drive current Ia is adjusted to reduce the light emission intensity (light emission characteristics) of the LED 21 to make an adjustment to satisfy the condition of expression (3).

If the judgement result indicates that the spectral products A1 and A2 satisfy the condition of expression (3), the control circuit 27 transmits a signal after the end of the adjustment of the spectral products to the control circuit 36 of the video processor 5 in step S7. The control circuit 36 then uses the standard white plate to execute a process of color balancing.

More specifically, based on brightness information of a brightness signal of the first image signal picked up under the first illuminating light and a brightness signal of the second image signal picked up under the second illuminating light outputted from the brightness detection circuit 34, the control circuit 36 adjusts the gain of at least one of the two variable gain amplifiers 38*a* and 38*b* in the color balance circuit 38 to make the two brightnesses equal.

Note that the respective output signals of the variable gain amplifiers 38*a* and 38*b* may be inputted to the control circuit 36, and the control circuit 36 may control and adjust the gains of the variable gain amplifiers 38*a* and 38*b* to make the signal levels of the respective output signals of the respective output signals of the variable gain amplifiers 38*a* and 38*b* equal.

Furthermore, for a value (for example, 1) on the basis of the gain of one of the variable gain amplifiers (for example, 38*a*), the gain of the other variable gain amplifier 38*b* may be adjusted to adjust (set) the color balance.

When the process of setting the color balance state in which the signal levels of the output signals of the variable gain amplifiers 38*a* and 38*b* are equal is finished, the adjustment process in the initial setting is finished, and the endoscopy can be started as shown in step S8. That is, the adjustment process in the initial setting of FIG. 4 is finished.

The operator then performs the endoscopy. The operator inserts the endoscope 3A into the subject 2 to start the endoscopy.

FIG. 5 shows a timing diagram for describing operation in performing the endoscopy. The LEDs 21 and 22 configured to respectively generate the first illuminating light and the second illuminating light in the light source apparatus 4 alternately repeat emitting the light and halting (turning off) the light emission. For example, in each first illumination period T1 of time periods t1 to t2 and t4 to t6, the LED 21 emits light, and the LED 22 is turned off. In each second illumination period T2 of time periods t2 to t4 and t6 to t8, the LED 22 emits light, and the LED 21 is turned off. In the times t2 and t6 at the end of the first illumination period T1, the CCD driver 31 outputs the CCD drive signal, and the CCD 14A outputs the first image pickup signal obtained by picking up an image of the subject 2. Note that although output periods (time periods t2 to t3 and t6 to t7) of the CCD drive signal are periods shorter than the illumination period T1 or T2 in the example shown in FIG. 5, equal periods may be set.

Similarly, in the times t4 and t8 at the end of the second illumination period T2, the CCD driver 31 outputs the CCD drive signal, and the CCD 14A outputs the second image pickup signal obtained by picking up an image of the subject 2 in output periods (time periods t4 to t5 and t8 to t9).

The first image pickup signal and the second image pickup signal are respectively converted to the first image signal and the second image signal by the CDS circuit 32 and are alternately stored in the first memory 37*a* and the second memory 37*b* through the A/D conversion circuit 33 and the multiplexer 35.

For example, the first image pickup signal of the time periods t2 to t3 and t6 to t7 becomes the first image signal and is stored in the first memory 37*a*.

The second image pickup signal of the time periods t4 to t5 and t8 to t9 becomes the second image signal and is stored in the second memory 37*b*.

The first memory 37*a* holds the first image signal of the time period t2 to t3 until the second memory 37*b* starts storing the second image signal of the time period t4 to t5. At the time in which the second memory 37*b* can output the second image signal, the first memory 37*a* and the second memory 37*b* output the first image signal (Ia1 in FIG. 5) and the second image signal (Sb1 in FIG. 5) synchronized with the time period t4 to t8 (=T1+T2) that is one frame period T, toward the color balance circuit 38 of a latter stage.

Note that the first memory 37*a* and the second memory 37*b* output the first image signal (Sa2 in FIG. 5) and the second image signal (Sb2 in FIG. 5) obtained by synchronizing the first image signal of the time period t6 to t7 and the second image signal of the time period t8 to t9 with a next frame period (time period from t8, not shown) to the color balance circuit 38 of the latter stage. The first image signal and the second image signal through the variable gain amplifiers 38*a* and 38*b* set to the gains in the color balance state by the color balance circuit 38 are outputted to the D/A conversion circuits 39*a* and 39*b*.

The first image signal and the second image signal outputted from the D/A conversion circuits 39*a* and 39*b* are inputted to the G and R channels of the color monitor 6, and the observation image formed by the first image and the second image is displayed on the display surface of the color monitor 6.

As described, the spectral products A1 and A2 are set to satisfy expression (3) in the present embodiment. Therefore, according to the present embodiment, an observation image with an excellent image quality equal to or greater than a predetermined image quality as a whole can be obtained. Therefore, the operator can observe the observation image to smoothly perform the treatment.

Although the illuminating light on the long wavelength side of the first illuminating light is used as the second illuminating light with respect to the first illuminating light in the case described in the first embodiment, the description can also be applied to a case of a first modification using third illuminating light on the short wavelength side of the first illuminating light, for example.

In this case, an LED 23 configured to generate third illuminating light can be arranged in FIG. 1, in place of the LED 22 configured to generate the second illuminating light. The LED 23 has, for example, the light emission intensity Ec as indicated by an alternate long and two short dashes line in FIG. 2.

Figure 6:
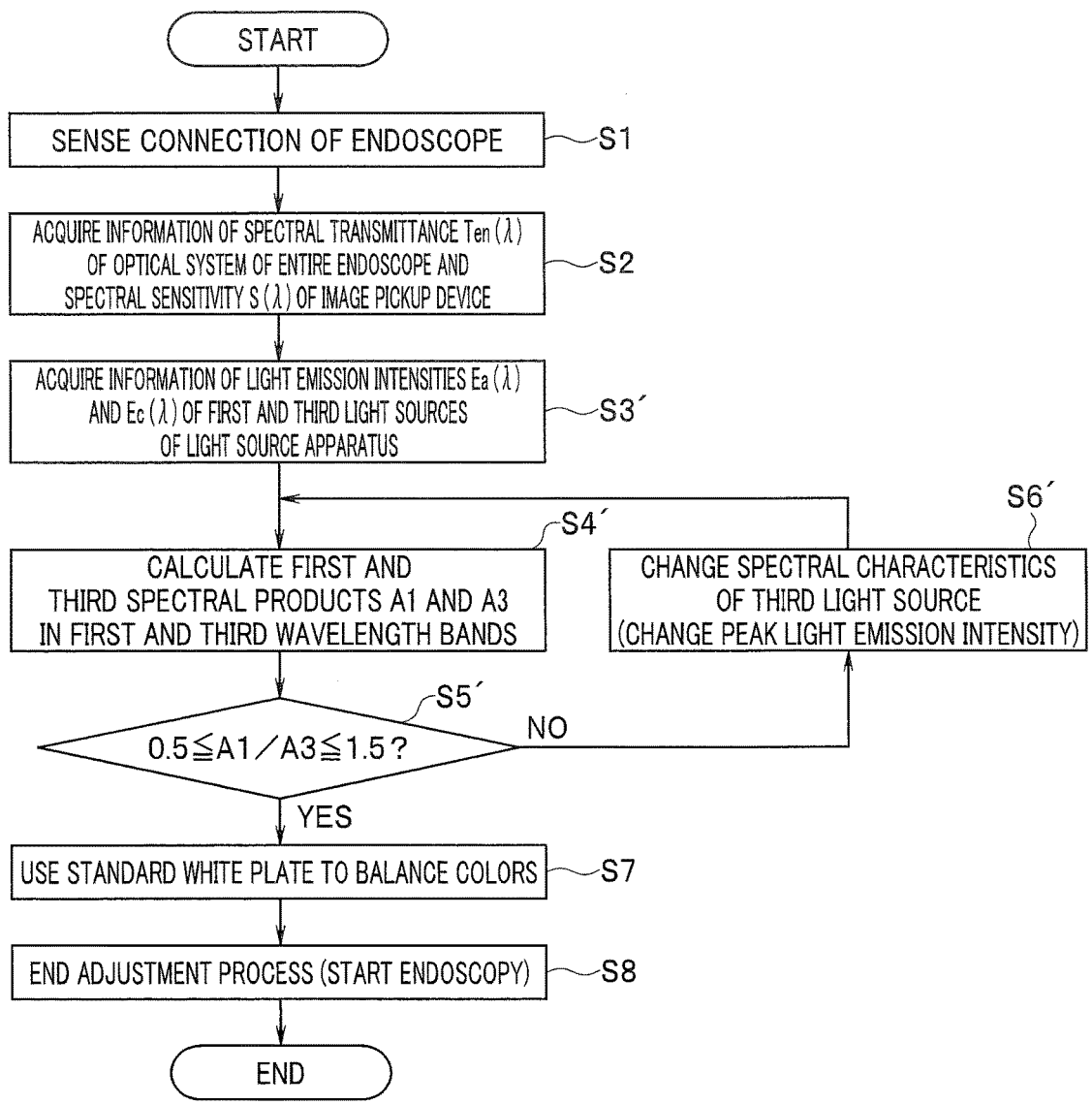
FIG. 6 is a flowchart showing content of adjustment before endoscopy in a first modification of the first embodiment.

In this case, the second memory 37b in FIG. 1 can store a third image signal corresponding to a third image pickup signal picked up under the illumination by the LED 23, and the third image signal outputted from the second memory 37b can be inputted to a channel B of the color monitor 6. In the case of the present modification, the adjustment process of FIG. 4 is as in FIG. 6. The process of FIG. 6 includes steps S3' to S6' in which second spectral product A2 in steps S3 to S6 in FIG. 4 are replaced by third spectral product A3, and the like, respectively.

More specifically, in step S3', "second light source" in step S3 of FIG. 4 is changed to "third light source", and "Eb (λ)" is changed to "Ec (λ)". In step S4', "second wavelength" in step S4 of FIG. 4 is changed to "third wavelength", and "second spectral product A2" is changed to "third spectral product A3".

In step S5', "A2" in step S5 of FIG. 4 is changed to "A3". That is, the control circuit 27 (the spectral product calculation circuit 27a of the control circuit 27) has a function of a judgement circuit configured to judge whether the following is satisfied.

$$0.5 \leq A1/A3 \leq 1.5 \quad (4)$$

In step S6', "second" in step S6 of FIG. 4 is changed to" changed to "third". The present modification has an effect similar to the first embodiment. The third illuminating light is on the short wavelength side of the first illuminating light, and the third illuminating light is suitable for figuring out the traveling state of the blood vessels near the surface layer. According to the present modification, an observation image with an excellent image quality suitable for figuring out the traveling state of the blood vessels near the surface layer can be acquired.

Next, an endoscope apparatus 1B of a second modification configured to use the first illuminating light, the second illuminating light, and the third illuminating light to acquire an observation image will be described.

Figure 7:
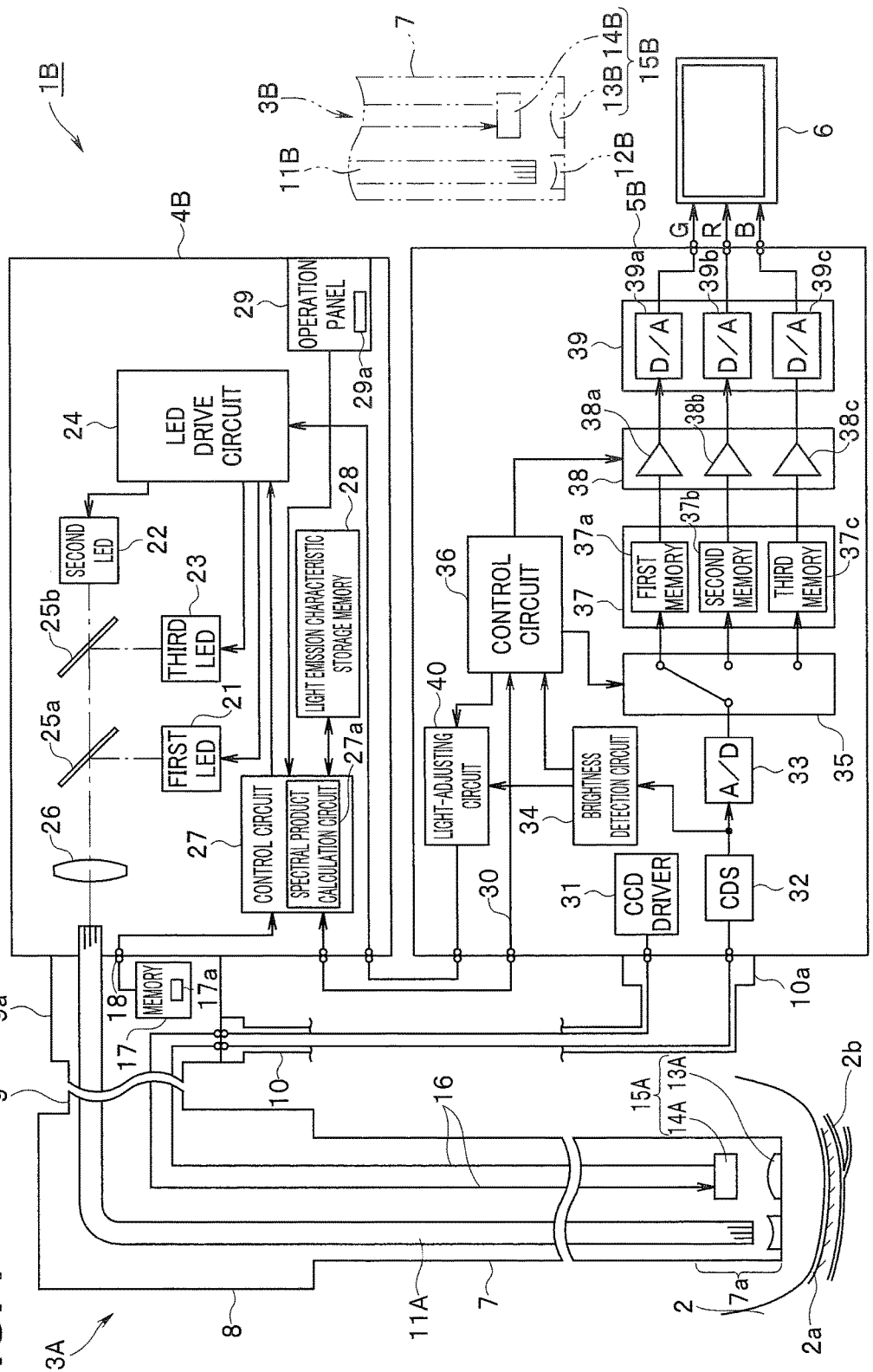
FIG. 7 is a diagram showing an overall configuration of an endoscope apparatus of a second modification of the first embodiment.

FIG. 7 shows a configuration of the endoscope apparatus 1B of the second modification. The endoscope apparatus 1B includes the endoscopes 3A and 3B, a light source apparatus 4B, a video processor 5B, and the color monitor 6.

The endoscope apparatus 1B includes the light source apparatus 4B further provided with the third LED 23, which is a third light source, and a dichroic mirror 25b in the light source apparatus 4 of the endoscope apparatus 1 of FIG. 1.

The third LED 23 configured to emit light based on a drive signal from the LED drive circuit 24 generates the third illuminating light formed by narrow band light of a third wavelength band having the light emission intensity Ec (λ) indicated by the alternate long and two short dashes line of FIG. 2. The light of the third wavelength band is selectively reflected by the dichroic mirror 25b arranged on an optical path of the third illuminating light and is selectively transmitted through the dichroic mirror 25a opposing on the reflected optical path. The light is condensed by the opposing condensing lens 26 and is caused to enter the light guide 11A.

The second illuminating light of the LED 22 is selectively transmitted through the dichroic mirror 25b arranged on the optical path and is further selectively transmitted through the dichroic mirror 25a as described above. The light is condensed by the opposing condensing lens 26 and is caused to enter the light guide 11A.

In the video processor 5B, the two-system image processing circuit in the video processor 5 of FIG. 1 is changed to a three-system image processing circuit.

More specifically, the multiplexer 35 configured to switch two contact points in the video processor 5 of FIG. 1 is changed to the multiplexer 35 configured to switch three contact points. The memory circuit 37 including the first and second memories 37a and 37b configured to store the first and second image signals is changed to the memory circuit 37 including first, second, and third memories 37a, 37b, and 37c configured to store the first, second, and third image signals.

The color balance circuit 38 including the variable gain amplifiers 38a and 38b configured to receive the first and second image signals from the memory circuit 37 in the video processor 5 of FIG. 1 is changed to the color balance circuit 38 including variable gain amplifiers 38a, 38b, and 38c configured to receive the first, second, and third image signals. The D/A conversion section 39 including the two D/A conversion circuits 39a and 39b is changed to the D/A conversion section 39 including three D/A conversion circuits 39a, 39b, and 39c. The video processor 5B is configured to input the third image signal outputted from the D/A conversion circuit 39c to the channel B of the color monitor 6.

In the present modification, the brightness detection circuit 34 detects the average brightness of the first and second image signals and detects average brightness of the third image signal. The brightness detection circuit 34 outputs each brightness signal to the light-adjusting circuit 40 and the control circuit 36.

In the present modification, the control circuit 27 of the light source apparatus 4B calculates the first and second spectral products A1 and A2 and performs the control operation of making an adjustment to satisfy the condition of expression (3). The control circuit 27 also calculates the third spectral product A3 in the case of image pickup using the third illuminating light of the third wavelength band and performs the control operation of adjusting the spectral characteristics of the third illuminating light to satisfy the condition of expression (4). Note that the spectral characteristic storage memory 28 also stores the information of the light emission characteristics of the LED 23 in addition to the information of the light emission characteristics of the LEDs 21 and 22 in the first embodiment. The spectral characteristic storage memory 28 also stores the information of the spectral transmittance Tls (λ) of the dichroic mirrors 25a and 25b and the condensing lens 26 in the light source apparatus 4B.

In the present modification, the control circuit 27 further judges whether the following condition is satisfied.

$$1/A3 \leq 1/A2 \text{ (or } 1 \leq A3/A2) \quad (5)$$

The control circuit 27 performs control operation of adjusting the spectral characteristics of the second or third illuminating light to satisfy the condition.

The other component is the same as the component described in the first embodiment, and the description will not be repeated.

The condition of expression (5) is set due to the following reason. The third illuminating light is a short wavelength band belonging to a blue wavelength band in the visible band. The spectral sensitivity S (λ) tends to decrease, and the third illuminating light tends to be affected by noise.

Therefore, the third spectral product A3 is set to be greater than the second spectral product A2 as in expression (5) to suppress the value of the gain of the variable gain amplifier 38c that is necessary for the color balance. In this way, an increase in the noise can be suppressed, and an excellent image quality can be secured. On the other hand, if the spectral product A3 is smaller than the spectral product A2, the value of the gain of the variable gain amplifier 38c needs to be greater than the value of the gain of the variable gain amplifier 38b in the color balancing.

Next, an adjustment process before the endoscopy in the present modification will be described with reference to FIG. 8.

Figure 8:
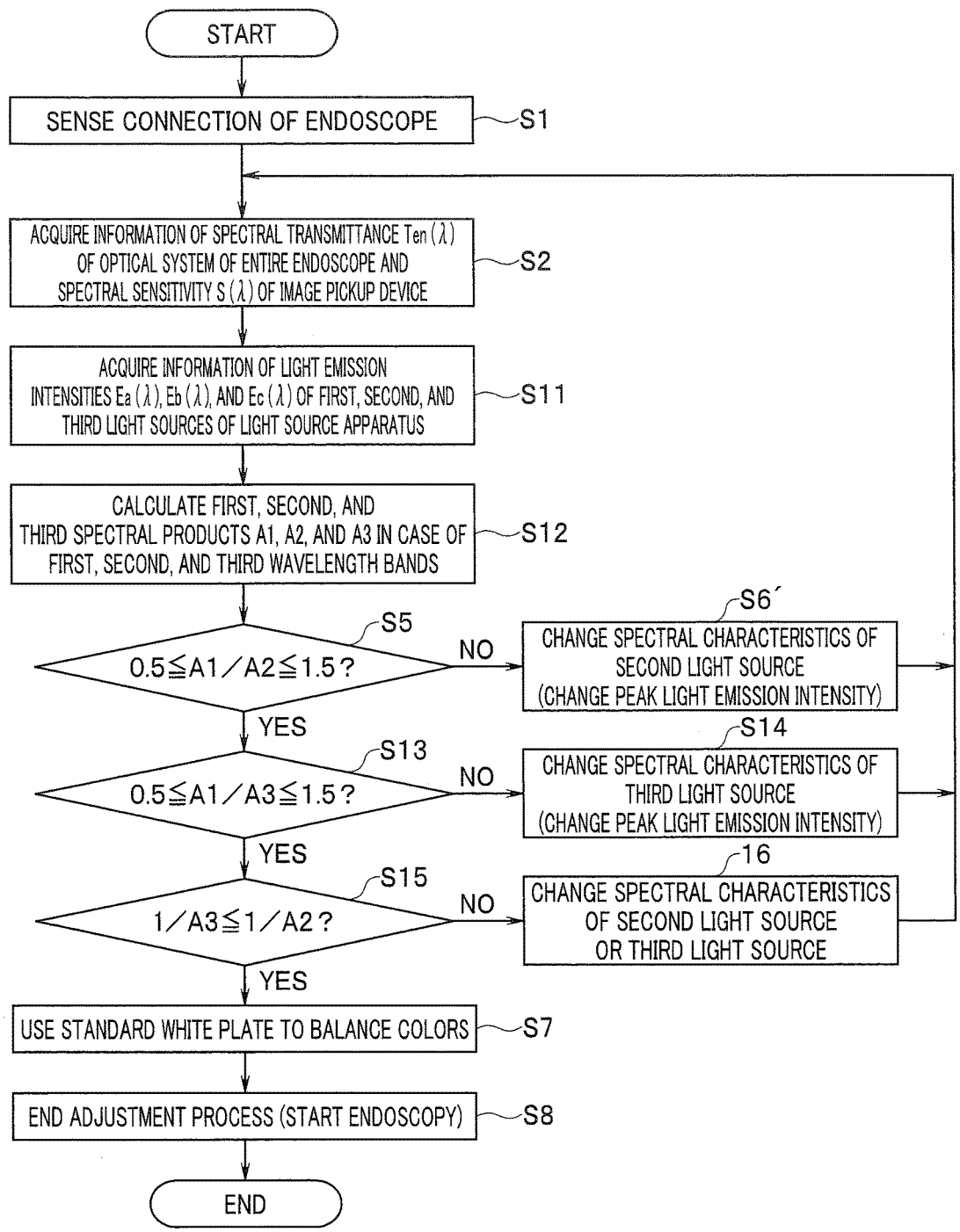
FIG. 8 is a flowchart showing content of adjustment before endoscopy of the second modification.

The processes of steps S1 and S2 in FIG. 8 are the same as the processes of steps S1 and S2 in FIG. 4. In step S11 following step S2, the control circuit 27 acquires the information of the light emission intensities Ea (λ), Eb (λ), and Ec (λ) of the LEDs 21, 22, and 23 respectively forming the first, second, and third light sources of the light source apparatus 4B from the light emission characteristic storage memory 28. The control circuit 27 also acquires the information of the spectral transmittance Tls (λ) of the optical system in the light source apparatus 4B from the light emission characteristic storage memory 28.

In next step S12, the control circuit 27 (the spectral product calculation circuit 27a of the control circuit 27) calculates the first, second, and third spectral products A1, A2, and A3 when the CCD 14A picks up images under the illuminating light of the first, second, and third wavelength bands.

In next step S5, the control circuit 27 judges whether the first and second spectral products A1 and A2 calculated in the previous step S12 satisfy the condition of expression (3), that is, $0.5 \leq A1/A2 \leq 1.5$.

If the judgement result indicates that the condition of expression (3) is not satisfied in the judgement process of step S5, the control circuit 27 changes the spectral characteristics, such as the light emission intensity Eb (λ) of the LED 22 that is the second light source, in step S6 and returns to the process of step S11. As described in FIG. 4, the control circuit 27 increases or decreases the drive current Ib to make an adjustment to satisfy the condition of expression (3). Note that when the adjustment cannot be made to satisfy the condition of expression (3) within the variable range of the drive current Ib, the control circuit 27 adjusts the drive current Ia to make an adjustment to satisfy the condition of expression (3).

If a judgement result satisfying the condition of expression (3) is obtained in step S5, the control circuit 27 judges in step S13 whether the first and third spectral products A1 and A3 calculated in step S12 satisfy the condition of expression (4), that is, $0.5 \leq A1/A3 \leq 1.5$.

If the judgement result indicates that the condition of expression (4) is not satisfied in the judgement process of step S13, the control circuit 27 in step S14 changes the spectral characteristics, such as the light emission intensity Eb (λ) of the LED 23 that is the third light source, and returns to the process of step S11. As described in FIG. 4, the control circuit 27 increases or decreases the drive current Ib to make an adjustment to satisfy the condition of expression (4). Note that when the adjustment cannot be made to satisfy the condition of expression (4) within the variable range of the drive current Ib, the control circuit 27 adjusts the drive current Ia to make an adjustment to satisfy the condition of expression (4).

If the judgement result indicates that the condition of expression (4) is satisfied in the judgement process of step S13, the control circuit 27 in step S15 judges whether the spectral products A2 and A3 satisfying expressions (3) and (4) in steps S5 and S13 satisfy the condition of expression (5), that is, $1/A3 \leq 1/A2$.

If the judgement result indicates that the condition of expression (5) is not satisfied in the judgement process of step S15, the control circuit 27 changes the spectral characteristics, such as the light emission intensity of the second light source or the third light source, in step S16 and returns to the process of step S11.

If the judgement result indicates that the condition of expression (5) is satisfied in the judgement process of step S15, the control circuit 27 uses the standard white plate to execute the process of color balancing in step S7 as in the case of FIG. 4.

However, in FIG. 4, based on the brightness information of the brightness signal of the first image signal picked up under the first illuminating light and the brightness signal of the second image signal picked up under the second illuminating light outputted from the brightness detection circuit 34, the control circuit 27 adjusts the gain of at least one of the two variable gain amplifiers 38a and 38b in the color balance circuit 38 to make the two brightnesses equal.

On the other hand, in the present modification, based on brightness information of a brightness signal of the third image signal picked up under the third illuminating light in addition to the brightness signal of the first image signal and the brightness signal of the second image signal outputted from the brightness detection circuit 34, the control circuit 27 adjusts at least two gains of the three variable gain amplifiers 38a, 38b, and 38c in the color balance circuit 38' to make the three brightnesses equal.

When the process of setting the color balance state in which the signal levels of the output signals of the variable gain amplifiers 38a, 38b, and 38c are equal is finished, the adjustment process in the initial setting is finished, and the endoscopy can be started as shown in step S8. That is, the adjustment process in the initial setting of FIG. 8 is finished.

Figure 9:
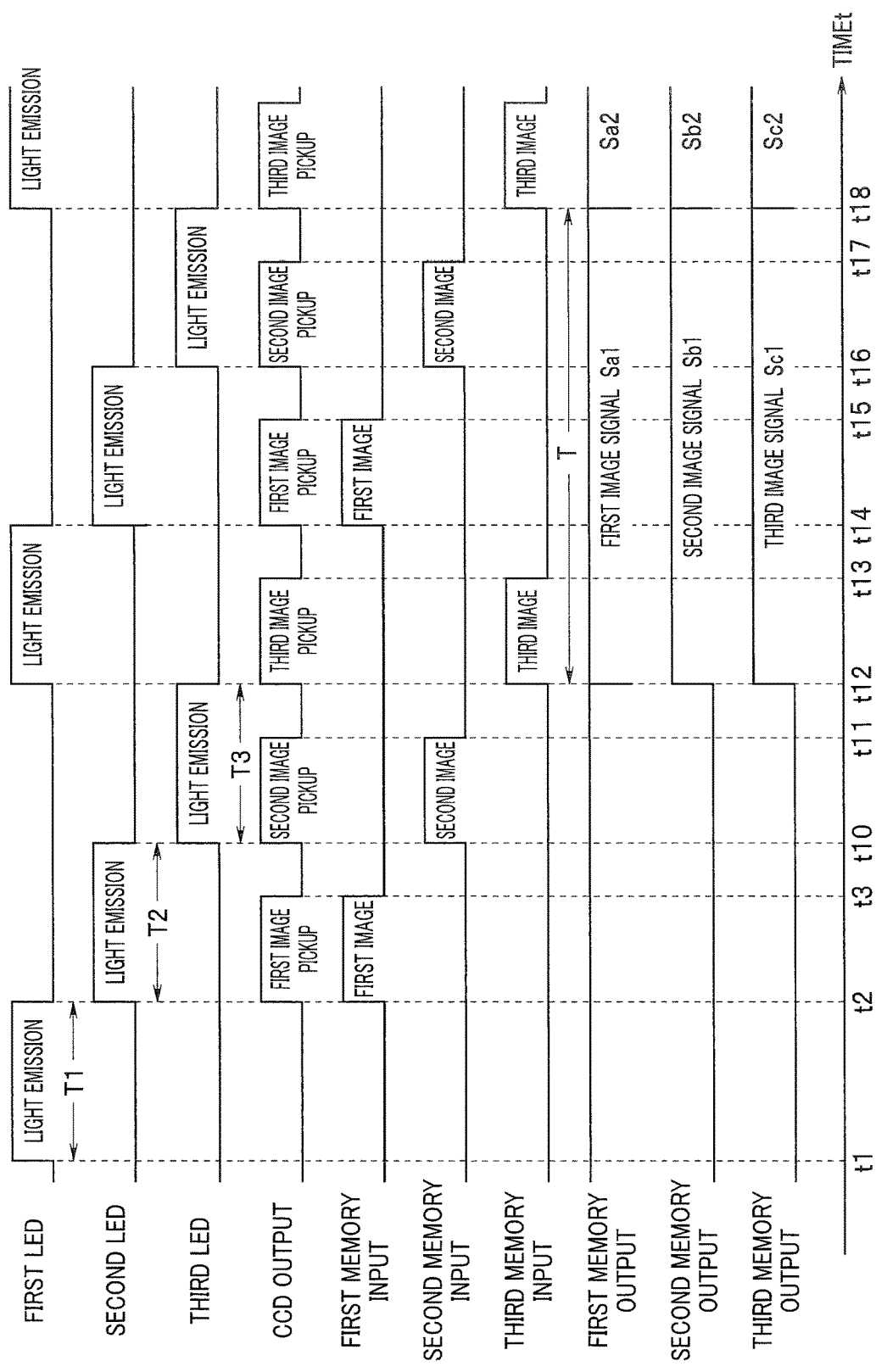
FIG. 9 is a timing diagram showing operation in performing the endoscopy in the second modification.

FIG. 9 shows a timing diagram describing operation in performing the endoscopy after the end of the process of color balancing in FIG. 8.

The timing diagram of FIG. 9 is a timing diagram in which the alternate light emission of the first and second illuminating light in the timing diagram of FIG. 5 is changed to sequential light emission of the first, second, and third illuminating light.

More specifically, the LED 21 is caused to emit light in the first illumination period T1 as in the first embodiment, and the LED 22 is caused to emit light in the second illumination period T2. In the present modification, the LED 23 is caused to emit light in a third illumination period T3 after the second illumination period T2 to sequentially cause the three LEDs 21, 22, and 23 to emit light. Note that respective illumination periods are equal, and T1=T2=T3.

As shown in FIG. 9, the LED 21 emits light in time periods t1 to t2, t12 to t14, . . . , the LED 22 emits light in time periods t2 to t10, t14 to 16, . . . , and the LED 23 emits light in time periods t10 to t12, t16 to t18, . . . .

The CCD driver 31 applies drive signals to the CCD 14A in synchronization with the end of the illumination periods Ti (i=1, 2, 3), and the CCD 14A sequentially outputs the first image pickup signal, the second image pickup signal, the third image pickup signal, the first image pickup signal, the second image pickup signal, . . . in the time periods t2 to t3, t10 to t11, t12 to 13, t14 to t15, t16 to t17 . . . .

As in the first embodiment, the first memory 37a and the second memory 37b store the first image signal and the second image signal corresponding to the first image pickup signal and the second image pickup signal, respectively. Furthermore, in the present modification, the third memory 37c stores the third image signal corresponding to the third image pickup signal.

The first memory 37a, the second memory 37b, and the third memory 37c synchronize the image signals acquired in the first illumination periods T1 (t1 to t2), T2 (t2 to t3), and T3 (t10 to t12) as shown in FIG. 9 and outputs the first image signal Sa1, the second image signal Sb1, and a third image signal Sc1 to the latter stage side in the time period t12 to t18 (=T1+T2+T3) that is one frame period T. Note that following the image signals, the image signals acquired in the next illumination periods T1 (t12 to t14), T2 (t14 to t16), and T3 (t16 to t18) are synchronized, and the first image signal Sa2, the second image signal Sb2, and a third image signal Sc2 are outputted at the same time.

The present modification has the same effect as the first embodiment. Note that in the first embodiment, an image with an excellent SNR can be acquired for the image quality of the observation image acquired in two different wavelength bands. On the other hand, according to the present modification, an image with an excellent SNR can be acquired for the image quality of the observation image acquired in three different wavelength bands.

Next, the second embodiment of the present invention will be described.

Second Embodiment

Figure 10:
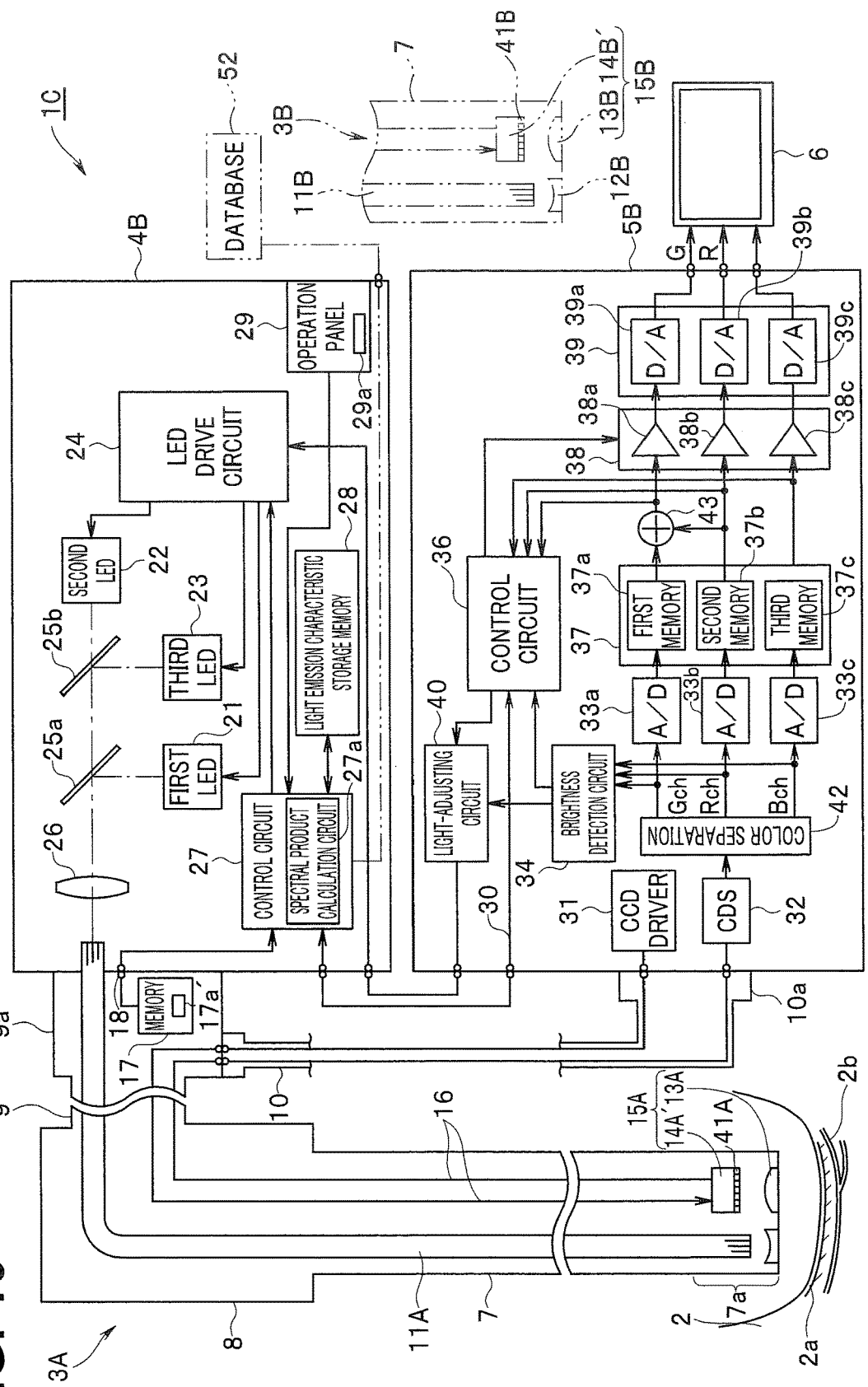
FIG. 10 is a diagram showing an overall configuration of an endoscope apparatus of a second embodiment of the present invention.

FIG. 10 shows a configuration of an endoscope apparatus 1C of the second embodiment of the present invention. Whereas the case of the endoscopes 3A and 3B including monochrome image pickup devices is described in the first embodiment (and the first modification), the present embodiment provides an endoscope including an image pickup device with color filters configured to optically separate colors.

As shown in FIG. 10, an endoscope apparatus 1C includes endoscopes 3A' and 3B', the light source apparatus 4B, a video processor 5C, and the color monitor 6.

The endoscope 3A' is provided with color filters 41A in front of the image pickup surface of the CCD 14A in the endoscope 3A of FIG. 1.

Figure 11:
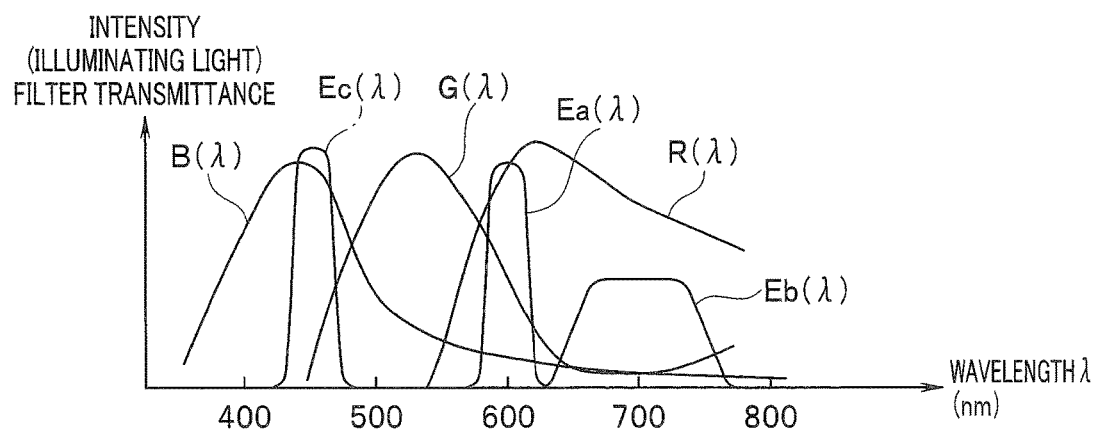
FIG. 11 is a diagram showing spectral characteristics of light emission intensities of respective light emitting elements of a light source section and transmittances of color filters of image pickup devices in the second embodiment.

FIG. 11 shows characteristics of spectral transmittances of an R filter 41r, a G filter 41g, and a B filter 41b included in the color filters 41A in the present embodiment. Note that the light emission intensities Ea ($\lambda$), Eb ($\lambda$), and Ec ($\lambda$) of the LEDs 21, 22, and 23 in FIG. 11 are the same as those shown in FIG. 2.

The endoscope 3B' includes color filters 41B with characteristics different from the color filters 41A in front of the image pickup surface of the CCD 14B in the endoscope 3B of FIG. 1.

A spectral information storage region 17a' in the flash memory 17 in the present embodiment stores information of the spectral transmittances of the color filters 41A in addition to the spectral information of the spectral information storage region 17a described above. Note that in the following description, reference sign 14A' will be used to describe the CCD including the color filters 41A. That is, a spectral sensitivity Sa' ($\lambda$) of the CCD 14A' is equal to characteristics obtained by multiplying the spectral sensitivity Sa ($\lambda$) of the CCD 14A by the spectral transmittances of the color filters 41A (that is, spectral transmittances of the R filter 41r, the G filter 41g, and the B filter 41b shown in FIG. 11 (indicated by R ($\lambda$), G ($\lambda$), and B ($\lambda$), respectively)). The spectral sensitivity Sa' ($\lambda$) roughly has characteristics including pixels with characteristics close to the spectral transmittance of the R filter 41r, pixels with characteristics close to the spectral transmittance of the G filter 41g, and pixels with characteristics close to the spectral transmittance of the B filter 41b.

Figure 12:
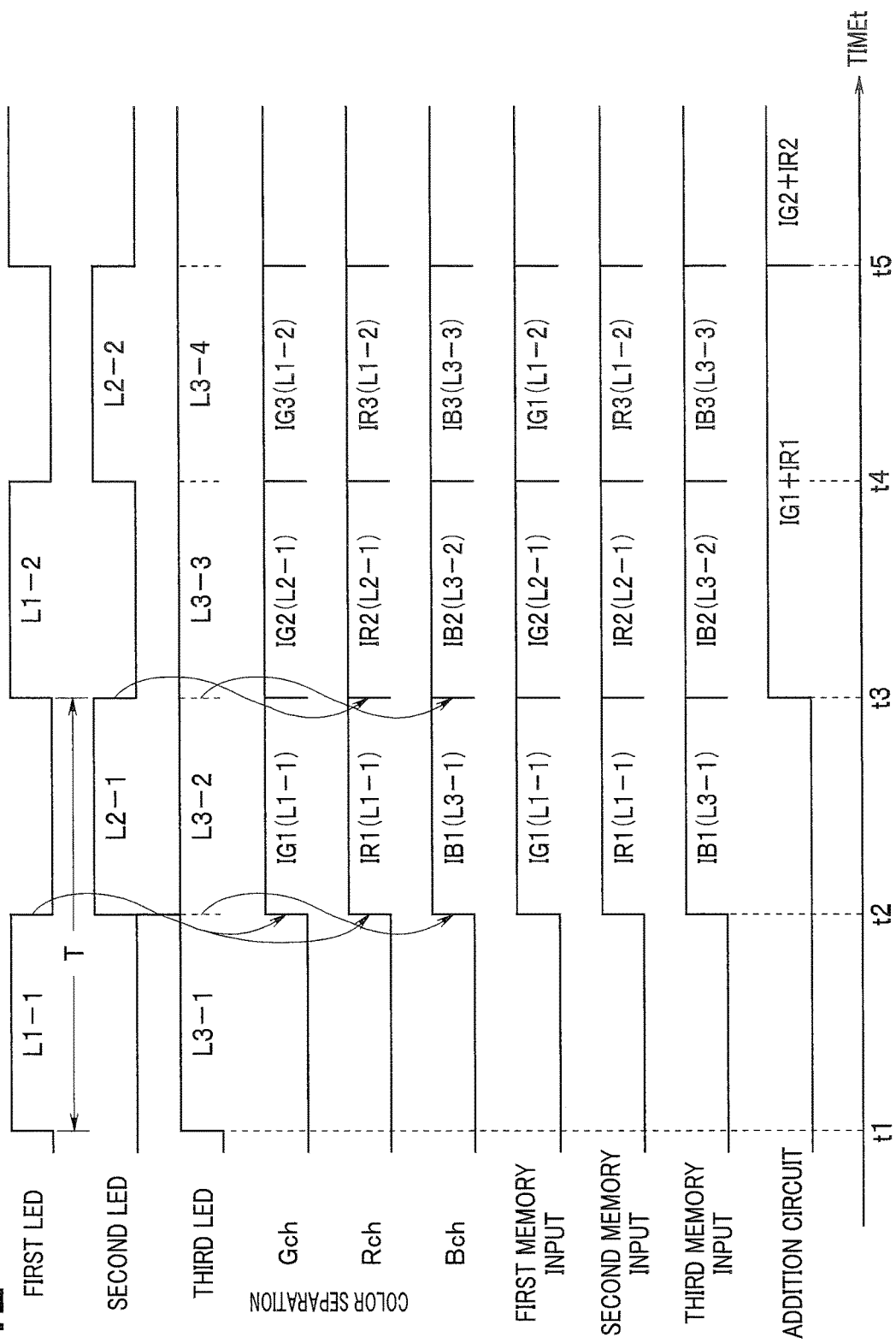
FIG. 12 is a timing diagram showing operation in performing endoscopy in the second embodiment.

In the present embodiment, the light source apparatus 4B has the same configuration as the light source apparatus 4B of FIG. 7. However, in the present embodiment, the LED drive circuit 24 causes the LED 21 and the LED 22 to alternately emit light and causes the LED 23 to emit light all the time (in other words, continuously emit light) as shown in FIG. 12. Note that in FIG. 12, illumination periods of the illuminating light L1 to L3 of an H level in the light emission by the LEDs 21 to 23 are indicated by providing information of an order of light emission.

For example, the first LED 21 performs first light emission (illumination) in the time period t1 to t2, and the light emission period (or illumination period) is indicated by L1-1. The first LED 21 performs second light emission in the time period t3 to t4, and the light emission period (or illumination period) is indicated by L1-2.

Similarly, the second LED 22 performs first light emission in the time period t2 to t3, and the light emission period (or illumination period) is indicated by L2-1. The second LED 22 performs second light emission in the time period t4 to t5, and the light emission period (or illumination period) is indicated by L2-2.

Although the third LED 23 emits light all the time, the third LED 23 performs first light emission in the time period t1 to t2, and the light emission period (or illumination period) is indicated by L3-1. The third LED 23 performs second light emission in the time period t2 to t3, and the light emission period (or illumination period) is indicated by L3-2.

The video processor 5C in the present embodiment executes signal processing corresponding to the image pickup device (the CCD 14A' in FIG. 10) including the color filters (41A in FIG. 10) connected to the video processor 5C.

An image pickup signal outputted from the CCD 14A' becomes an image signal in which signal components are extracted through the CDS circuit 32. A color separation circuit 42 separates the image signal into image signals of three channels R, G, and B according to the array of the R filter 41r, the G filter 41g, and the B filter 41b in the color filters 41A.

The image signals of the channels G, R, and B (abbreviated as Gch, Rch, and Bch in FIG. 10) separated by the color separation circuit 42 are inputted to A/D conversion circuits 33a, 33b, and 33c and the brightness detection circuit 34.

FIG. 12 specifically shows the image signals of the channels G, R, and B. For example, in a period of the start of the first illumination period L2-1 of the second illuminating light L2 of the LED 22 after the end of the first illumination period L1-1 of the first illuminating light L1 of the LED 21, the color separation circuit 42 outputs, to the latter stage side, each of IG1 (L1-1) as an image signal of the channel G, IR1 (L1-1) as an image signal of the channel R, and IB1 (L3-1) as an image signal of the channel B.

In a period of the start of the second illumination period L1-2 of the first illuminating light L1 of the LED 21 after the end of the first illumination period L2-1 of the second illuminating light L2 of the LED 22, the color separation circuit 42 outputs, to the latter stage side, each of IG2 (L2-1) as an image signal of the channel G, IR2 (L2-1) as an image signal of the channel R, and IB2 (L3-2) as an image signal of the channel B.

Note that in the present embodiment, when return light from the subject 2 is received under the illuminating light of the first illuminating light L1, an addition circuit 43 described below adds the image signal of the channel G and the image signal of the channel R to generate an image signal of the channel G in consideration of main spectral characteristics of FIG. 11.

The digital image signals converted by the A/D conversion circuits 33a, 33b, and 33c are stored in the first memory 37a, the second memory 37b, and the third memory 37c of the memory circuit 37, respectively.

The image signals synchronized by the first memory 37a, the second memory 37b, and the third memory 37c of the memory circuit 37 are inputted to the variable gain amplifiers 38a, 38b, and 38c of the color balance circuit 38 through the addition circuit 43 and are also inputted to the control circuit 36.

For example, the image signal IG1 (L1-1) of the channel G, the image signal IR1 (L1-1) of the channel R, and the image signal IB1 (L3-1) of the channel B outputted from the color separation circuit 42 in the period of the start of the illumination period L2-1 are stored in the first memory 37a, the second memory 37b, and the third memory 37c, respectively, as indicated by first memory input, second memory input, and third memory input in FIG. 12.

The image signal IG2 (L2-1) of the channel G, the image signal IR2 (L2-1) of the channel R, and the image signal IB1 (L3-2) of the channel B outputted from the color separation circuit 42 in the period of the start of the illumination period L1-2 following the illumination period L2-1 are stored in the first memory 37a, the second memory 37b, and the third memory 37c, respectively, as indicated by the first memory input, the second memory input, and the third memory input in FIG. 12.

The first memory 37a, the second memory 37b, and the third memory 37c synchronize the image signals stored in the illumination period L1-1 and the illumination period L2-1 and output the image signals. In this case, signal levels of the image signals IG1 (L1-1) and IR1 (L1-1) acquired in the case of the first illuminating light L1 are greater than the signal levels of the image signals IG2 (L2-1) and IR2 (L2-1) in the case of the second illuminating light L2. Therefore, the addition circuit adds the image signals IG1 (L1-1) and IR1 (L1-1) and outputs the signal as shown in FIG. 12 (abbreviated as IG1+IR1 in FIG. 12). Note that the image signal in the case of the second illuminating light L2 is approximated only to IR2 (L2-1).

Operation following the time t4 after the end of the illumination period L1-2 is repetition of the operation of a cycle T that is the time period t2 to t4 after the end of the illumination period L1-1.

The gains of the variable gain amplifiers 38a, 38b, and 38c of the color balance circuit 38 are adjusted by using the standard white plate as described in the first embodiment. In the present embodiment, the added image signal is adopted as the image signal of the channel G. Therefore, the control circuit 36 refers to the added image signal of the channel G to adjust the gains of the three variable gain amplifiers 38a, 38b, and 38c.

The three image signals outputted from the color balance circuit 38 are inputted to the channels G, R, and B of the color monitor 6 through the three D/A conversion circuits 39a, 39b, and 39c of the D/A conversion section 39. The observation image in the traveling state of the blood vessels near the surface layer of the biological tissue of the subject 2 picked up by the CCD 14A' is displayed as an endoscopic image on the display surface of the color monitor 6.

The other component is substantially the same as the first embodiment.

The adjustment process before the execution of the endoscopy in the present embodiment is almost the same as the process shown in FIG. 8.

However, the spectral sensitivity Sa ($\lambda$) in the first spectral product A1 of equation (1) in the present embodiment, $$A1 = \int Sa(\lambda) Ea(\lambda) Tls(\lambda) Ten(2) d\lambda \qquad (1),$$

is replaced by the spectral sensitivity Sa' ($\lambda$), and this is approximated by $$Sa'(\lambda) \approx G(\lambda) + R(\lambda).$$

The timing diagram of the operation in the case of performing the endoscopy after the end of the adjustment process is as shown in FIG. 12.

The present embodiment has the same effect as the first embodiment. According to the present embodiment, in the case of the image pickup under the first illuminating light L1, the process of using the addition signal to generate the observation image is executed by considering the characteristics of the spectral transmittances of the R filter 41r, the G filter 41g, and the B filter 41b in the color filters 41A. Therefore, an observation image with an excellent SNR for the image quality can be generated.

The characteristics of the LEDs in the light source apparatus are mainly adjusted to satisfy expression (3), expression (4), and expression (5) by considering the characteristics of the actually used image pickup devices and the like of the endoscope in the case of the illuminating light of a plurality of wavelength bands generated by the actually used light source apparatus in the actually used endoscope apparatus 1 or the like in the embodiments.

On the other hand, as described below, optical information in various endoscopes and various light source apparatuses may be registered in a database, and an operator of a hospital who performs endoscopy may determine a combination of an endoscope and a light source apparatus suitable for conditions for performing the endoscopy from a plurality of endoscopes and a plurality of light source apparatuses possessed by the hospital.

FIG. 13 shows a process of determining an endoscope and a light source apparatus suitable for performing predetermined endoscopy.

For example, a database creator of a manufacturer records optical characteristics of various endoscopes and various light source apparatuses manufactured by the manufacturer in a hard disk apparatus or the like forming a database apparatus and creates a database of the optical characteristics in first step S21. The database of the database apparatus can be referenced through a communication line, the Internet, or the like.

In next step S22, the operator who intends to perform predetermined endoscopy in the hospital sets (inputs) a wavelength band W1 of the first illuminating light L1, a second wavelength band W2 of the second illuminating light L2, and a third wavelength band W3 of the third illuminating light L3 used in the predetermined endoscopy in the database apparatus from a keyboard or the like of a terminal apparatus in order to acquire information suitable for the predetermined endoscopy from the database apparatus. Note that an operation panel provided on the light source apparatus or an operation panel provided on the video processor may be used as the terminal apparatus.

In next step S23, the database apparatus extracts the light source apparatuses corresponding to the conditions of the illuminating light of step S22 and displays the light source apparatuses on a display apparatus of a terminal apparatus or the like. Note that the color monitor 6 may be used as the display apparatus. The operator extracts the light source apparatuses possessed by the hospital from a list of the light source apparatuses displayed on the display apparatus and sets candidates of usable light source apparatuses. Note that when one usable light source apparatus exists, the usable light source apparatus is determined.

In next step S24, the database apparatus extracts the endoscopes corresponding to the conditions of the illuminating light of step S22 and displays the endoscopes on the display apparatus of the terminal apparatus or the like. The operator extracts the endoscopes possessed by the hospital from a list of the endoscopes displayed on the display apparatus and sets as candidates of usable endoscopes. Note that when one usable endoscope exists, the usable endoscope is determined.

In next step S25, the operator makes an input to calculate the spectral products in each wavelength band of the illuminating light L1, L2, and L3 for the usable light source apparatuses (candidates) and the usable endoscopes (candidates). The calculated spectral products are displayed on the display apparatus.

In this case, the operator may make an input to the database apparatus so that the database apparatus calculates the spectral products. A program for calculating the spectral products may be mounted on the terminal apparatus, and the terminal apparatus may calculate the spectral products.

In next step S26, the operator extracts a combination of the light source apparatus and the endoscope most appropriately satisfying expression (3), expression (4), and expression (5) regarding the calculated spectral products. The operator sets the light source apparatus and the endoscope as the light source apparatus and the endoscope to be actually used in the endoscope apparatus that performs the predetermined endoscopy. The process of FIG. 13 ends. Note that when the light of two wavelength bands is used to perform the predetermined endoscopy, a combination of the light source apparatus and the endoscope satisfying expression (3) or expression (4) may be extracted or selected.

As a result of FIG. 13, the combination of the light source apparatus and the endoscope most appropriately satisfying expression (3), expression (4), and expression (5) can be selected from the usable light source apparatuses and endoscopes and used for the endoscopy. Therefore, the image quality of the observation image more appropriately generated by using the light of a plurality of wavelength bands can be improved as a whole.

As a result of FIG. 13, when a plurality of usable endoscopes exist for example, the information of the spectral sensitivity $S(\lambda)$ of the image pickup device mounted on each endoscope and the spectral transmittances $T(\lambda)$ of the light guide and the like are included to calculate each spectral product A. Therefore, the setting can be more easily performed to appropriately satisfy expression (3), expression (4), and expression (5) compared to when the setting is mainly performed to satisfy expression (3), expression (4), and expression (5) only from the spectral characteristics in the light source apparatus as in the first embodiment.

Even when the conditions of expression (3) and expression (4) are stricter, the setting can also be easily performed to satisfy the conditions. For example, when a plurality of combinations satisfying expression (3) exist, a combination satisfying a condition stricter than expression (3) may be determined.

For example, when a plurality of endoscopes or a plurality of light source apparatuses satisfying $C \leq A1/A2 \leq D$ exist, wherein $0.5 < C$ and $1.5 > D$, a combination of the endoscope and the light source apparatus with a smallest value of D−C may be determined and adopted.

Note that in a case of using one light source apparatus and performing the predetermined endoscopy using the light source apparatus, when a plurality of endoscopes usable for the predetermined endoscopy exist as a result of accessing the database apparatus from the light source apparatus (for example, the endoscope 3B of FIGS. 1 and 10), an endoscope more appropriately satisfying expression (3), expression (4), expression (5), and the like may be used to perform in the endoscopy.

For example, as indicated by an alternate long and two short dashes line in FIG. 10, the control circuit 27 of the light source apparatus 4 can access a database apparatus 52 through a communication line 51. When the light of a plurality of wavelength bands is used to perform the predetermined endoscopy by using the light source apparatus 4, an endoscope suitable for the execution of the endoscopy can be selected to determine the endoscope apparatus, and the image quality of the observation image obtained by the endoscope apparatus can be improved as a whole.

Note that in the calculation of the spectral products A1, A2, and the like in the embodiments and the like, the spectral products may be calculated only for the endoscopes with large individual differences based on the types of endoscope.

Embodiments formed by partially combining the embodiments and the like also belong to the present invention.

What is claimed is:

1. An endoscope apparatus comprising:
a light source section configured to generate light of a first wavelength band emitted to a subject having hemoglobin, the light of the first wavelength band having spectral characteristics of a narrow band between a wavelength including a maximum value and a wavelength including a minimum value on light absorption characteristics of the hemoglobin in a red band of a visible wavelength band, the light source section also configured to generate light of a second wavelength band in which scattering characteristics in the subject and absorption characteristics of the hemoglobin are lower than in the light of the first wavelength band, the light of the second wavelength band including a wavelength band that is a wavelength longer than the light of the first wavelength band;
an image pickup section configured to receive light from the subject irradiated with the light from the light source section to generate an image pickup signal;
an image generation section configured to generate an observation image of the subject from a first image pickup signal generated by receiving light from the subject irradiated with the light of the first wavelength band and a second image pickup signal generated by receiving light from the subject irradiated with the light of the second wavelength band in the image pickup section; and a control section configured to control a spectral product of at least one of the light of the first wavelength band and the light of the second wavelength band from the light source section to the image pickup section such that a first spectral product from the light source section to the image pickup section in the first wavelength band falls into a condition that is 50% to 150% of a second spectral product from the light source section to the image pickup section in the second wavelength band.

2. The endoscope apparatus according to claim 1, wherein the control section controls a light emission intensity of at least one of the light of the first wavelength band and the light of the second wavelength band to control the spectral product of at least one of the light of the first wavelength band and the light of the second wavelength band to satisfy the condition.

3. The endoscope apparatus according to claim 1, wherein the light of the second wavelength band is light in a band wider than the light of the first wavelength band and is light in the red or near-infrared band.

4. The endoscope apparatus according to claim 1, wherein the light source section further generates light of a third wavelength band including a visible wavelength band on a short wavelength side of the light of the first wavelength band, the image generation section generates an observation image of the subject from the first image pickup signal, the second image pickup signal, and a third image pickup signal generated by receiving light from the subject irradiated with the light of the third wavelength band in the image pickup section, and the control section further controls a spectral product of at least one of the light of the first wavelength band, the light of the second wavelength band, and the light of the third wavelength band from the light source section to the image pickup section such that the first spectral product A1, the second spectral product A2, and a third spectral product A3 from the light source section to the image pickup section in the third wavelength band satisfy a following second condition $1/A3 \leq 1/A2$.

5. The endoscope apparatus according to claim 1, wherein the endoscope apparatus comprises: first and second endoscopes comprising first and second image pickup sections, respectively, as the image pickup section formed by first and second image pickup devices with different image pickup sensitivities, respectively; and a light source apparatus to which the first or second endoscope is detachably connected, the light source apparatus including a light source section incorporating a first light emitting element configured to generate the light of the first wavelength band and a second light emitting element configured to generate the light of the second wavelength band, and the control section comprises a spectral product calculation section configured to read characteristics of the image pickup sensitivity of the first or second image pickup section mounted on the first or second endoscope connected to the light source apparatus from an information storage section storing the characteristics of the image pickup sensitivities, and further refers to information of light emission characteristics of the first light emitting element and the second light emitting element to calculate the first and second spectral products.

6. The endoscope apparatus according to claim 5, further comprising a database apparatus configured to store a database of information of spectral characteristics with respect to respective wavelengths, the information including information of spectral characteristics of a plurality of endoscopes with different image pickup sensitivities of the image pickup sections or different spectral transmittances of light guides for guiding the light of the first and second wavelength bands and information of spectral characteristics of the light source section with light emission characteristics for generating the light of the first and second wavelength bands, wherein when the light of the first and second wavelength bands is used to perform predetermined endoscopy, the control section executes a process of referring to the database to select an endoscope satisfying the condition.

7. The endoscope apparatus according to claim 5, further comprising a database apparatus configured to store a database of information of respective spectral characteristics of a plurality of endoscopes with different image pickup sensitivities of the image pickup sections or different spectral transmittances of light guides for guiding the light of the first and second wavelength bands and information of respective spectral characteristics of a plurality of light source apparatuses respectively including light source sections with different light emission characteristics of the first and second light emitting elements configured to respectively generate the light of the first and second wavelength bands, wherein when the light of the first and second wavelength bands is used to perform predetermined endoscopy, the control section refers to the database to select a combination of an endoscope and a light source apparatus satisfying the condition.

* * * * *